(12) United States Patent
Dennis et al.

(10) Patent No.: US 12,110,489 B2
(45) Date of Patent: Oct. 8, 2024

(54) GENE SITE SATURATION MUTAGENESIS (GSSM) METHOD

(71) Applicant: BASF SE, Ludwigshafen am Rhein (DE)

(72) Inventors: Jared Dennis, San Diego, CA (US); Xuqiu Tan, San Diego, CA (US); Robin Cai, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 442 days.

(21) Appl. No.: 16/954,092

(22) PCT Filed: Dec. 18, 2018

(86) PCT No.: PCT/US2018/066294
§ 371 (c)(1),
(2) Date: Jun. 16, 2020

(87) PCT Pub. No.: WO2019/126211
PCT Pub. Date: Jun. 27, 2019

(65) Prior Publication Data
US 2022/0251540 A1    Aug. 11, 2022

Related U.S. Application Data

(60) Provisional application No. 62/608,167, filed on Dec. 20, 2017.

(51) Int. Cl.
*C12N 15/10* (2006.01)
*C12N 1/20* (2006.01)
*C12N 15/70* (2006.01)

(52) U.S. Cl.
CPC ........... *C12N 15/1031* (2013.01); *C12N 1/20* (2013.01); *C12N 15/70* (2013.01); *C12N 2800/101* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 6,171,820 B1 * | 1/2001 | Short | C12N 9/00 506/10 |
| 6,562,594 B1 | 5/2003 | Short | |
| 6,764,835 B2 | 7/2004 | Short | |
| 7,202,086 B2 | 4/2007 | Delcourt et al. | |
| 9,476,078 B2 | 10/2016 | Tan | |
| 2009/0130718 A1 | 5/2009 | Short | |
| 2009/0312196 A1 | 12/2009 | Colbeck et al. | |

FOREIGN PATENT DOCUMENTS

| WO | WO-02/16606 A2 | 2/2002 |
|---|---|---|
| WO | WO-2009/088933 A1 | 7/2009 |
| WO | WO2009/152336 A1 | 12/2009 |
| WO | WO2014/189287 A1 | 11/2014 |

OTHER PUBLICATIONS

International Search Report & Written Opinion ISA, PCT/US2018/066294 (Mar. 22, 2019).
European Search Report for EP Patent Application No. 18891128.3. Issued on Oct. 5, 2021, 4 pages.
Jones, et al., "Comparison of Five Protein Engineering Strategies for Stabilizing an α/β-Hydrolase", Biochemistry, vol. 56, Issue 50, Oct. 31, 2017, pp. 6521-6532.
International Search Report for PCT Patent Application No. PCT/US2018/066294, Issued on Mar. 22, 2019, 4 pages.
Levy, et al., "Quantitation of supercoiled circular content in plasmid DNA solutions using a fluorescence-based method", Nucleic Acids Research, vol. 28, Issue 12, Jun. 15, 2000, 7 pages.
Needleman, et al., "A General Method Applicable to the Search for Similarities in the Amino Acid Sequence of Two Proteins", Journal of Molecular Biology, vol. 48, Mar. 28, 1970, pp. 443-453.
Pearson, et al., "Improved tools for biological sequence comparison", Proceedings of the National Academy of Sciences of the United States of America, vol. 85, Issue 8, Apr. 1, 1988, pp. 2444-2448.
Smith, et al., "Comparative biosequence metrics", Journal of Molecular Evolution, vol. 18, Jan. 1981, pp. 38-46.
Smith, et al., "Comparison of biosequences", Advances in Applied Mathematics, vol. 2, 1981, pp. 482-489.
Smith, et al., "Identification of Common Molecular Subsequences", Journal of Molecular Biology, vol. 147, Mar. 25, 1981, pp. 195-197.
Smith, et al., "Overlapping Genes And Information Theory", Journal of Theoretical Biology, vol. 91, Issue 2, 1981, pp. 379-380.
Yakov Gluzman, "SV40-transformed simian cells support the replication of early SV40 mutants", Cell, vol. 23, Issue 1, Jan. 1981, pp. 175-182.

* cited by examiner

*Primary Examiner* — Kaijiang Zhang
(74) *Attorney, Agent, or Firm* — Armstrong Teasdale LLP

(57) ABSTRACT

Disclosed herein is an improved Gene Site Saturation Mutagenesis (GSSM) method for producing a plurality of modified polynucleotides and/or polypeptides, creating specific changes to a gene, and reassembling mutations or changes at one or more sites.

42 Claims, 5 Drawing Sheets

Specification includes a Sequence Listing.

```
  1 GATACACTGGAGAGC ATTGACAACTGCGGC GTGGGCTGCCCGACC GGCGGTTCTAGCAAT GTTAGTATCGTCCGC
  1 D   T   L   E   S   I   D   N   C   A   V   G   C   P   T   G   G   S   S   N   V   S   I   V   R
 76 CATGGCGTATACTCTG AATAACAACTCCACC AATTGCCAAC TGGGTGGCCGTATCAC ATTACTAAAGACACA
 26 H   A   Y   T   L   N   N   N   S   T   K   F   A   N   W   V   A   Y   H   I   T   K   D   T
151 CCTGCGTCAGGCAAG ACTCGTAATTGGAAA ACTGATCCAGCGTTG AATCCTGCTGACACC CTGGCTCCGGCGGAT
 51 P   A   S   G   K   T   R   N   W   K   T   D   P   A   L   N   P   A   D   T   L   A   P   A   D
226 TATACCGGCGCTAAT GCCGCTCTTAAAGTG GATCGTGGGCACCAG GCGCCGTTGCCAGC CTGGCGGGTGTTTCA
 76 Y   T   G   A   N   A   A   L   K   V   D   R   G   H   Q   A   P   L   A   S   L   A   G   V   S
301 GACTGGGAAAAGCCTG AATTACCTCTCAAAC AGTGATCTGAATCAA ATCACGCCGCAGAAA GGCGCGTGGGCCCGT
101 D   W   E   S   L   N   Y   L   S   N   S   D   L   N   Q   I   T   P   Q   K   G   A   W   A   R
376 CTGGAGGATCAGGAG CGCAAACTTATCGAT CGTGCAGATATTAGT AGTGTGTATACTGTC ACGGGCCCACTGTAC
126 L   E   D   Q   E   R   K   L   I   D   R   A   D   I   S   S   V   Y   T   V   T   G   P   L   Y
451 GAACGTGATATGGGC AAACTCCCGGGCACC CAGAAAGCTCACACT ATTCCGTCTGCGTAC TGGAAAGTGATCTTT
126 E   R   D   M   G   K   L   P   G   T   Q   K   A   H   T   I   P   S   A   Y   W   K   V   I   F
151                                                                                      
526 ATTAACAACTCCCCG GCCGGTGAATCATTAC GCTGCCGTTTTTGTT GATCAGAACACCCCA AAAGGGGGGATTTC
151 I   N   N   S   P   A   V   N   H   Y   A   A   F   L   F   D   Q   N   T   P   K   G   A   D   F
176                                                                                      
601 TGCCAGTTTCGTGTT ACCGTTGATGAAATT GAAAAACGCACAGGC TTAATTATCTGGCG GCCCTGCCAAATGAC
176 I   N   N   S   P   A   V   N   H   Y   A   A   F   L   F   D   Q   N   T   P   K   G   A   D   F
201 C   Q   F   R   V   T   V   D   E   I   E   K   R   T   G   L   I   I   W   A   G   L   P   N   D
676 GTCCAGGCGCGTCCTTG AAATCCAAGCCGGGC GTGCTGCCGGAACTG ATGGGTTGCAAAAAC (SEQ ID NO: 1)
201                                                                   (SEQ ID NO: 2)
226 V   Q   A   S   L   K   S   K   P   G   V   L   P   E   L   M   G   C   K   N
```

FIG. 1

GENE SITE SATURATION MUTAGENESIS (GSSM) METHOD

INCORPORATION BY REFERENCE TO ANY PRIORITY APPLICATIONS

The present application is a U.S. National Phase Application of International Patent Application No. PCT/US18/66294, filed Dec. 18, 2018, which claims priority to U.S. Provisional Application No. 62/608,167, filed on Dec. 20, 2017, the entire contents of which are hereby expressly incorporated by reference in their entirety.

REFERENCE TO SEQUENCE LISTING

The present application is being filed along with a Sequence Listing in electronic format. The Sequence Listing is provided as a file entitled 150212US02_SequenceListingForFiling.TXT, created Oct. 2, 2021, which is 24 kb in size. The information in the electronic format of the Sequence Listing is incorporated herein by reference in its entirety.

BACKGROUND

Field

The present disclosure relates generally to gene modification, including gene mutagenesis methods for producing a plurality of modified polynucleotides, producing modified polypeptides, and making specific modifications to genes.

Description of the Related Art

Genetic modifications are important for research, agricultural, industrial, and medical applications. A variety of gene modification techniques have been introduced. Published and commercial gene modification methods include, for example, error-prone PCR, Invitrogen's Gene Tailor site-directed Mutagenesis Kit™, Stratagene's QuickChange Mutagenesis Kit™, overlap PCR, and PCR-based ligation/recombination. However, many of these techniques can be laborious and expensive to use, and some of them may result in biased codon frequency in the modified genes. Therefore, there is still a need for more effective methods which can efficiently generate specific gene variants with technical simplicity.

SUMMARY

Described herein include methods, compositions and systems for producing modified polynucleotides from a parent polynucleotide; and methods, compositions and systems for producing modified polypeptides for a parent polypeptide.

Disclose herein include a method of producing a plurality of modified polynucleotides from a parent polynucleotide comprising the coding region of a subject protein, wherein each of the plurality modified polynucleotides encode a modified polypeptide that comprises an amino acid substitution at a first amino acid position of interest in the protein of interest. In some embodiments, the method comprises: (a) providing a plurality of primers capable of binding to a desired region of the parent polynucleotides, wherein the desired region comprises the codon for the amino acid at the first position of interest of the subject protein, wherein at least N of the plurality of primers each comprise a first codon for a different alternative amino acid at the first amino acid position of interest, wherein N is the number of desired amino acid substitutions at the first position of interest; (b) contacting the plurality of primers with the parent polynucleotide to form a reaction mixture; and (c) subjecting the reaction mixture to a polymerase extension reaction to generate the plurality of modified polynucleotides.

In some embodiments, at least one of the plurality of primers comprises a second codon for one of the alternative amino acids. In some embodiments, the plurality of primers comprises at least two or more primers each comprising a second codon for a different alternative amino acid. In some embodiments, N is an integer between 1 and 19. In some embodiments, N is 19.

In some embodiments, the plurality of polynucleotides comprises polynucleotides that encode for polypeptides having all possible standard amino acid substitutions at the first amino acid position of interest as compared to the subject protein. In some embodiments, the plurality of primers does not comprise degenerate primers.

In some embodiments, the method further comprises designing the plurality of primers based on the sequence of the desired region of the parent polynucleotide.

In some embodiments, at least one of the plurality of primers is capable of binding to a region between 20 nucleotides upstream and 20 nucleotides downstream of the codon for the amino acid at the first amino acid position of interest.

In some embodiments, the method further comprises treating the plurality of modified polynucleotides generated in step (c) with a restriction enzyme to remove the parent polynucleotide. In some embodiments, the method further comprises recovering the plurality of modified polynucleotides. In some embodiments, the method further comprises introducing one or more of the modified polynucleotides to a host cell to express one or more mutants of the subject protein.

In some embodiments, at least one of the codons in the primers for the different alternative amino acids at the first amino acid position of interest is a preferred codon of the host cell.

In some embodiments, the method further comprises analyzing the one or more mutants of the subject protein for stability, pH, product inhibition, salt tolerance, thermostability, substrate specificity, activity, stereoselectivity, expression (e.g., expression pattern or expression level), pH profile change (e.g., change to higher or lower pH), co-factor specificity, product inhibition, salt tolerance, sensitivity to salt concentration, sensitivity to salt, binding affinity, or a combination thereof. In some embodiments, the method further comprises selecting one or more mutants of the subject protein based on their stability, thermostability, substrate specificity, activity, stereoselectivity, expression (e.g., expression pattern or expression level), pH profile change (e.g., change to higher or lower pH), co-factor specificity, product inhibition, salt tolerance, sensitivity to salt concentration, sensitivity to salt, binding affinity, or a combination thereof.

In some embodiments, the host cell is a eukaryotic cell or a prokaryotic cell. In some embodiments, the host cell is a cell from an organism selected from the group consisting of *Pichia pastoris, Bacillus licheniformis, Bacillus subtilis, Pseudomonas fluorescens, Myceliopthora thermophile* fungus, *Aspergillus niger, Trichoderma reesei*, and *Escherichia coli*.

In some embodiments, the parent polynucleotide is a circular double-stranded DNA. In some embodiments, the plurality of primers comprises at least M additional primers each comprising codon for a different alternative amino acid at a second amino acid position of interest of the subject protein, wherein M is the number of desired amino acid substitutions at the second position of interest. In some embodiments, M is an integer between 1 and 19. In some embodiments, M is 19.

In some embodiments, at least one of the plurality of modified polynucleotides encodes a polypeptide comprising an amino acid substitution at the second amino acid position of interest. In some embodiments, the plurality of polynucleotides comprises polynucleotides that encode for polypeptides having all possible standard amino acid substitutions at the second amino acid position of interest as compared to the subject protein.

Also disclosed herein includes a method of producing a plurality of modified polypeptides of a parent polypeptide, wherein each of the plurality of modified polypeptide comprises an amino acid substitution at a first amino acid position of interest. In some embodiments, the method comprises: providing a plurality of primers capable of binding to a desired region of a template polynucleotide encoding the parent polypeptide, wherein the desired region comprises the codon for the amino acid at the first amino acid position of interest in the parent polypeptide, wherein at least N of the plurality of primers each comprise a first codon for a different alternative amino acid for the amino acid at the first amino acid position of interest, wherein N is the number of desired amino acid substitutions at the first position of interest; contacting the plurality of primers with the template polynucleotide to form a reaction mixture; subjecting the reaction mixture to a polymerase extension reaction to generate the plurality of modified polynucleotides; and introducing the modified polynucleotides to a recombinant expression system to produce the plurality of modified polypeptides.

In some embodiments, at least one of the plurality of primers comprises a second codon for one of the alternative amino acids. In some embodiments, the plurality of primers comprises at least two or more primers each comprising a second codon for a different alternative amino acid. In some embodiments, the plurality of primers comprises at least two or more primers each comprising a second codon for a different alternative amino acid. In some embodiments, N is an integer between 1 and 19. In some embodiments, N is 19.

In some embodiments, the plurality of polynucleotides comprises polynucleotides that encode for polypeptides having all possible standard amino acid substitutions at the first amino acid position of interest as compared to the parent polypeptide. In some embodiments, the plurality of primers does not comprise degenerate primers.

In some embodiments, the method further comprises designing the plurality of primers based on the sequence of the desired region. In some embodiments, at least one of the plurality of primers is capable of binding to a region between 20 nucleotides upstream and 20 nucleotides downstream of the codon for the amino acid at the first amino acid position of interest.

In some embodiments, the recombinant expression system is a host cell. In some embodiments, the host cell is a eukaryotic cell or a prokaryotic cell. In some embodiments, at least one of the codons in the primers for the different alternative amino acids at the first amino acid position of interest is a preferred codon of the host cell. In some embodiments, at least one of the codons in the primers for the different alternative amino acids at the first amino acid position of interest is the most preferred codon for an amino acid in the host cell.

In some embodiments, the method further comprises analyzing one or more of the modified polypeptides for stability, thermostability, substrate specificity, activity, stereoselectivity, expression (e.g., expression pattern or expression level), pH profile change (e.g., change to higher or lower pH), co-factor specificity, product inhibition, salt tolerance, sensitivity to salt concentration, sensitivity to salt, binding affinity, or a combination thereof. In some embodiments, the method further comprises selecting one or more mutants of the subject protein based on their stability, thermostability, substrate specificity, activity, stereoselectivity, expression (e.g., expression pattern or expression level), pH profile change (e.g., change to higher or lower pH), co-factor specificity, product inhibition, salt tolerance, sensitivity to salt concentration, sensitivity to salt, binding affinity, or a combination thereof.

In some embodiments, the template polynucleotide is a circular double-stranded DNA. In some embodiments, the plurality of primers comprises at least M additional primers each comprising codon for a different alternative amino acid at a second amino acid position of interest of the subject protein, wherein M is the number of desired amino acid substitutions at the second position of interest. In some embodiments, M is an integer between 1 and 19. In some embodiments, M is 19.

In some embodiments, at least one of the plurality of modified polypeptides comprises an amino acid substitution at the second amino acid position of interest. In some embodiments, the plurality of modified polynucleotides have all possible standard amino acid substitutions at the second amino acid position of interest as compared to the parent polypeptide.

BRIEF DESCRIPTION OF THE DRAWINGS

FIG. 1 shows the nucleic acid sequence (SEQ ID NO: 1) and protein sequence (SEQ ID NO: 2) of a nuclease selected as a gene of interest in Example 1.

DETAILED DESCRIPTION

Figure 2:
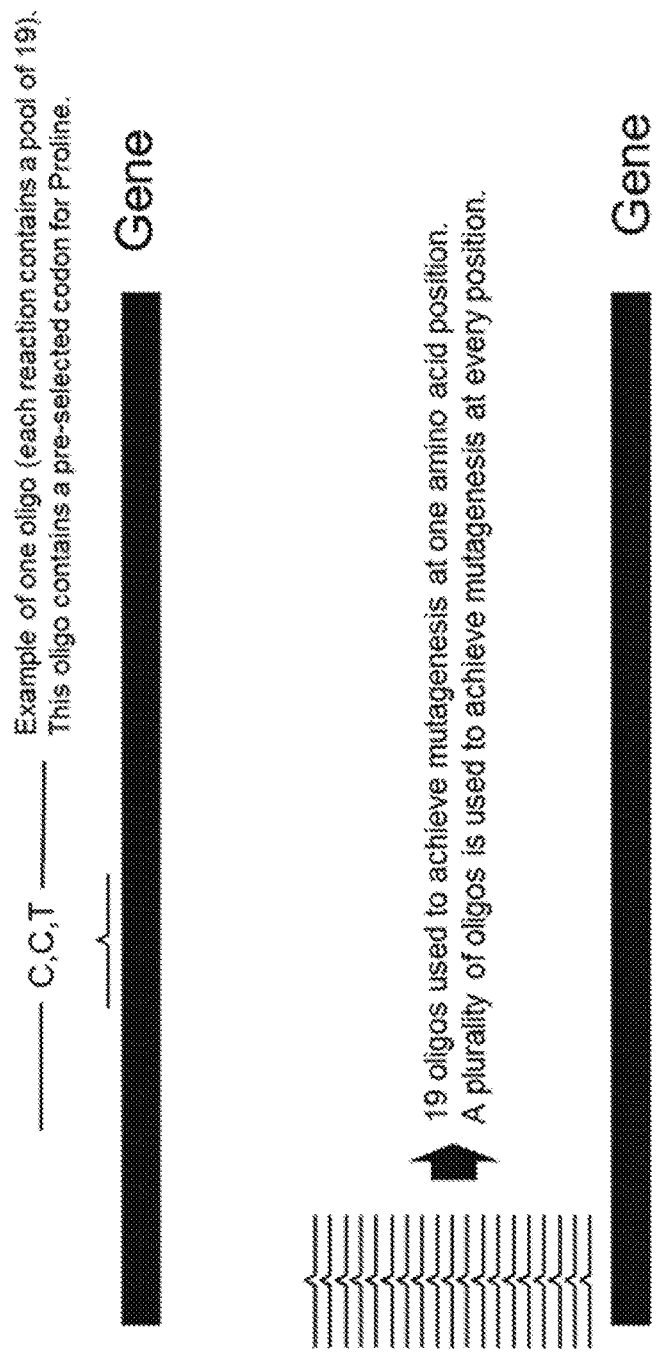
FIG. 2 is a schematic illustration of a non-limiting embodiment of the Gene Saturation Site-Directed Mutagenesis (GSSM) method disclosed herein. A pool of 19 preselected oligonucleotides ("oligos") each comprising codon for a different one of the 19 alternative amino acids at a target amino acid position is used to achieve mutagenesis at the target position in a gene of interest.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, the singular forms "a", "an", and "the" include plural references unless indicated otherwise, expressly or by context. For example, "a" dimer includes one or more dimers, unless indicated otherwise, expressly or by context.

The term "amplification" ("a polymerase extension reaction") means that the number of copies of a polynucleotide is increased.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend-0.5 and matrix=EBLOSUM62). The preferred alignment for the purpose of this invention is that alignment, from which the highest sequence identity can be determined.

For purposes of this description, percent identity is calculated by: %–identity=(identical residues/length of the alignment region which is showing the respective sequence of this invention over its complete length)*100. Thus, sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity".

For calculating the percent identity of two DNA sequences the same applies as for the calculation of percent identity of two amino acid sequences with some specifications. For DNA sequences encoding for a protein the pairwise alignment shall be made over the complete length of the coding region from start to stop codon excluding introns. For non-protein-coding DNA sequences the pairwise alignment shall be made over the complete length of the sequence of this invention, so the complete sequence of this invention is compared to another sequence, or regions out of another sequence. Moreover, the preferred alignment program implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNAFULL). Means for making these adjustments are well known to persons skilled in the art. For example, alignment for purposes of determining percent (%) sequence identity can be achieved in various ways that are within the skill in the art, for instance, using publicly available computer methods and programs such as BLAST, BLAST-2, ALIGN, FASTA (available in the Genetics Computing Group (GCG) package, from Madison, Wisconsin, USA), or Megalign (DNASTAR). Those of skill in the art can determine appropriate parameters for measuring alignment, including any algorithms needed to achieve maximal alignment over the full length of the sequences being compared.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

A "primer" is defined herein as a nucleic acid strand that can anneal to a template nucleic acid and serves as a starting point for DNA amplification. The primer can be entirely or partially complementary to a specific region of the template polynucleotide, for example 20 nucleotides upstream or downstream from a codon of interest. A non-complementary nucleotide is defined herein as a mismatch. A mismatch may be located within the primer or at the either end of the primer. Preferably, a single nucleotide mismatch, more preferably two, and more preferably, three or more consecutive or not consecutive nucleotide mismatches is (arc) located within the primer. The primer has from 5 to 200 nucleotides, preferably, from 20 to 80 nucleotides, and more preferably, from 43 to 65 nucleotides. More preferably, the primer has 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, or 190 nucleotides. A "forward primer" as defined herein is a primer that is complementary to a minus strand of the template polynucleotide. A "reverse primer" as defined herein is a primer complementary to a plus strand of the template polynucleotide. Preferably, the forward and reverse primers do not comprise overlapping nucleotide sequences. "Do not comprise overlapping nucleotide sequences" as defined herein means that a forward and reverse primer does not anneal to a region of the minus and plus strands, respectively, of the template polynucleotide in which the plus and minus strands are complimentary to one another. With regard to the primers annealing to the same strand of the template polynucleotide, "do not comprise overlapping nucleotide sequences" means the primers do not comprise sequences complementary to the same region of the same strand of the template polynucleotide. As used herein, a "primer set" may be used to mean a combination of a "forward primer" and a corresponding "reverse primer."

As used herein, the plus strand equivalent to the sense strand and may also be referred to as a coding or non-template strand. This is the strand that has the same sequence as the mRNA (except it has Ts instead of Us). The other strand, called the template, minus, or antisense strand, is complementary to the mRNA.

As described herein, "codon optimization" refers to the design process of altering codons to codons known to increase maximum protein expression efficiency. In some alternatives, codon optimization for expression in a cell is described, wherein codon optimization can be performed by using algorithms that are known to those skilled in the art so as to create synthetic genetic transcripts optimized for high mRNA and protein yield in hosts of interest, for example mammalian cells (e.g., human cells), fungal cells, insect cells, bacterial cells, eukaryotic cells, or prokaryotic cells. Codons can be optimized for protein expression in a bacterial cell, mammalian cell, yeast cell, insect cell, or plant cell, for example. Programs containing algorithms for codon optimization in humans are readily available. Such programs can include, for example, OptimumGene™ or GeneGPS® algorithms. Additionally codon optimized sequences can be obtained commercially, for example, from Integrated DNA Technologies. In some embodiments, the genes are codon optimized for expression in bacterial, yeast, fungal or insect cells.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction may be electrophoresed on a gel.

An enzyme is a biological molecule comprising a sequence of amino acids, wherein the enzyme can catalyze a reaction. Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors. Enzymes are also known as a polypeptide, a protein, a peptide, an amino acid sequence, or is identified by a SEQ ID NO. In this disclosure, the alternative names for enzyme can be used interchangeably.

"Recombinant" enzymes refer to enzymes produced by recombinant DNA techniques, i.e., produced from cells transformed by an exogenous DNA construct encoding the desired enzyme. A "synthetic" or "artificial" compound is produced by in vitro chemical or enzymatic synthesis. It includes, but is not limited to, variant nucleic acids made with optimal codon usage for host organisms, such as a yeast cell host or other expression hosts of choice or variant protein sequences with amino acid modifications, such as e.g. substitutions, compared to the parent protein sequence, e.g. to optimize properties of the polypeptide.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoRI site) or an immediately adjacent cleavage site (e.g. /CCWGG in the EcoRII site). In other cases, relevant restriction enzymes (e.g. the Eco57I site or CTGAAG (16/14)) contain a low ambiguity sequence (e.g. the CTGAAG sequence in the Eco57I site) with an external cleavage site (e.g. in the N16 portion of the Eco57I site). When an enzyme (e.g. a restriction enzyme) is said to "cleave" a polynucleotide, it is understood to mean that the restriction enzyme catalyzes or facilitates a cleavage of a polynucleotide.

An "ambiguous base requirement" in a restriction site refers to a nucleotide base requirement that is not specified to the fullest extent, i.e. that is not a specific base (such as, in a non-limiting exemplification, a specific base selected from A, C, G and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wunsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

The term "gene" means the segment of DNA involved in producing a polypeptide chain; it includes regions preceding and following the coding region (leader and trailer) as well as intervening sequences (introns) between individual coding segments (exons).

The term "heterologous" (or exogenous or foreign or recombinant) polypeptide is defined herein as:
(a) a polypeptide that is not native to the host cell. The protein sequence of such a heterologous polypeptide is a synthetic, non-naturally occurring, "man made" protein sequence;
(b) a polypeptide native to the host cell in which structural modifications, e.g., deletions, substitutions, and/or insertions, have been made to alter the native polypeptide; or
(c) a polypeptide native to the host cell whose expression is quantitatively altered or whose expression is directed from a genomic location different from the native host cell as a result of manipulation of the DNA of the host cell by recombinant DNA techniques, e.g., a stronger promoter.

Descriptions b) and c), above, refer to a sequence in its not naturally expressed by the cell used for its production. The produced polypeptide is therefore more precisely defined as a "recombinantly expressed endogenous polypeptide", which is not in contradiction to the above definition but reflects the specific situation that it's not the sequence of a protein being synthetic or manipulated but the way the polypeptide molecule is produced.

Similarly, the term "heterologous" (or exogenous or foreign or recombinant) polynucleotide refers:
(a) to a polynucleotide that is not native to the host cell;
(b) a polynucleotide native to the host cell in which structural modifications, e.g., deletions, substitutions, and/or insertions, have been made to alter the native polynucleotide;
(c) a polynucleotide native to the host cell whose expression is quantitatively altered as a result of manipulation of the regulatory elements of the polynucleotide by recombinant DNA techniques, e.g., a stronger promoter; or
(d) a polynucleotide native to the host cell, and integrated in a non-natural genetic environment as a result of genetic manipulation by recombinant DNA techniques.

With respect to two or more polynucleotide sequences or two or more amino acid sequences, the term "heterologous" is used to characterize that the two or more polynucleotide sequences or two or more amino acid sequences do not occur naturally in the specific combination with each other.

The term "isolated" means that the DNA is incorporated into a vector, such as a plasmid or viral vector; a nucleic acid that is incorporated into the genome of a heterologous cell (or the genome of a homologous cell, but at a non-naturally occurring site); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

"Ligation" refers to the process of forming phosphodiester bonds between nucleic acid strands (Sambrook et al, 1982, p. 146; Sambrook, 1989). DNA ligase can link together two DNA strands that have single-strand breaks (a break in both complementary strands of DNA). The alternative, a double-strand break, is fixed by a different type of DNA ligase using the complementary strand as a template but still requires DNA ligase to create the final phosphodiester bond to fully repair the DNA. Unless otherwise provided, ligation may be accomplished using known buffers and conditions with 10 units of T4 DNA ligase ("ligase") per 0.5 µg of approximately equimolar amounts of the DNA fragments to be ligated. "Products are not ligated" refers to not forming phosphodiester bonds between the ends of a nucleic acid obtained by amplifying the whole circular double-stranded template polynucleotide by using primers.

The term "mutations" is defined as alterations in the genetic code of a nucleic acid sequence or alterations in the sequence of a peptide. Such mutations may be point mutations such as transitions or transversions. A mutation may be a change to one or more nucleotides or encoded amino acid sequences. The mutations may be substitutions, deletions, insertions, or duplications.

As used herein, the degenerate "N,N,N" nucleotide sequence represents triplets, wherein "N" can be A, C, G or T. In some embodiments, the degenerate "N,N,N' nucleotide sequence is not TAG, TAA, or TGA.

The term "non-naturally occurring" refers to a (poly) nucleotide, amino acid, (poly)peptide, enzyme, protein, cell, organism, or other material that is not present in its original environment or source.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally. Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule." In addition, by way of example, but not limitation, a nucleic acid molecule that is labeled with a detectable moiety, such as a radioactive or alternatively a non-radioactive label, is likewise considered a "nucleic acid molecule."

The terms "nucleic acid sequence coding for" or a "DNA coding sequence of" or a "nucleotide sequence encoding" a particular protein or polypeptide refer to a DNA sequence which is transcribed and translated into a protein or polypeptide when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated and transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding a protein or peptide" or "DNA encoding a protein or peptide" or "polynucleotide encoding a protein or peptide" and other synonymous terms encompasses a polynucleotide which includes only coding sequence for the protein or peptide as well as a polynucleotide which includes additional coding and/or non-coding sequence.

Accordingly, in a non-limiting embodiment, a "nucleic acid library" is comprised of a vector-based collection of one or more nucleic acid molecules. In another preferred embodiment, a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

Any source of nucleic acid, in purified form can be utilized as the starting nucleic acid (also defined as "a template polynucleotide"). Thus, the process may employ DNA or RNA including messenger RNA, which DNA or RNA can be single-stranded, and preferably double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs, and more preferably from 50-11000 base pairs.

The nucleic acid may be obtained from any source, for example, from plasmids such a pBR322, from cloned DNA or RNA or from DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR, see U.S. Pat. Nos. 4,683,202 and 4,683,195). Alternatively, the polynucleotide may be present in a vector present in a cell and sufficient nucleic acid may be obtained by culturing the cell and extracting the nucleic acid from the cell by methods known in the art.

As used herein the term "parental polynucleotide set" is a set comprised of one or more distinct polynucleotide species. Usually this term is used in reference to a progeny polynucleotide set which is preferably obtained by mutagenization of the parental set, in which case the terms "parental, "starting and "template" are used interchangeably.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., Mg++, Ca++); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris-HCl, pH 5-8, with optional addition of divalent cation(s) and/or metal chelators and/or non-ionic detergents and/or membrane fractions and/or anti-foam agents and/or scintillants.

Standard convention (5' to 3') is used herein to describe the sequence of double-stranded polynucleotides.

The term "related polynucleotides" means that regions or areas of the polynucleotides are identical and regions or areas of the polynucleotides are heterologous.

The term "wild-type" means that the polynucleotide or peptide does not comprise any mutations.

As used herein, the term "amino acid," as used herein refers to any organic compound that contains an amino group (—NH2) and a carboxyl group (—COOH); preferably either as free groups or alternatively after condensation as part of peptide bonds. The "standard amino acids" are understood in the art and refer to proteinogenic amino acids that are encoded directly by triplet codons in the genetic code. The twenty standard amino acids are: alanine (ala or A), arginine (arg or R), asparagine (asn or N), aspartic acid (asp or D), cysteine (cys or C), glutamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

Gene site saturation mutagenesis (GSSM) is a comprehensive technique that systematically explores minimally all possible single amino acid substitutions along a protein sequence. Currently, GSSM method has been used to introduce point mutations into every position within a target gene using degenerate primer sets containing 32 or 64 codons to generate a complete library of variants. GSSM methods achieve a range of codon substitutions, comprising the 32 codons represented by the degenerate cassette sequence NNK or NNN, to achieve all possible amino acid changes at each amino acid site. This degenerate cassette sequence is added to the coding sequence at the position to be mutagenized. Unlike rational mutagenesis, GSSM does not require prior knowledge of the structure, or mechanism of a target protein due to its ability to generate all mutations at all positions within the protein. This technique can be used for directed evolution of enzymes with improved activity, stability, and stereoselectivity as well as improved binding properties of antibodies and transcription factors.

However, as with other directed evolution approaches, genetic selection is not a viable option when relying upon saturation mutagenesis. Therefore, time-consuming and costly screening must be performed to discover the most desirable mutations for a sequence of interest. The costs of screening for modified genes (i.e., variants) produced by GSSM grow exponentially in time and resources as the number of randomized positions increases. Relying upon degenerate codons such as NNN (where N=A/C/G/T), which requires 64 codons, produces a great deal of redundancy. Further, several codons are stop codons that inhibit screening. One solution to the problem of redundancy and premature stop codons is to use degenerate codons such as NNK (where K=G/T) or NNS (where S=C/G). GSSM often requires oversampling of the variants and creates a bias toward certain amino acid changes that may not be the best performing mutations. In addition, the earlier GSSM methods relying on degeneracies did not allow for a library to be exclusively comprised of preferential codons. GSSM has been disclosed in, for example, U.S. Pat. Nos. 6,171,820; 6,562,594; 6,764,835; and 9,476,078 (content of each of these references is incorporated herein by reference).

Described herein include a new and improved GSSM method, which is referred herein as "GSSM 2.2." GSSM 2.2 can produce a range of codon substitutions that cover some or all possible amino acid changes at each amino acid site of a subject protein. GSSM 2.2 achieves this through a pool of predesigned oligonucleotides containing non-degenerate cassette sequences coding for one or more pre-selected codons representing each desired alternative amino acid change. As shown in FIG. 2, oligonucleotides comprising codons for each possible mutated residue at every amino acid position over the full length of a protein-coding gene can be used. The codons in the predesigned oligonucleotides are, in some embodiments, optimized for protein expression of alternative amino acids for an expression host system of interest.

Method of Producing Modified Polynucleotides

Disclosed herein include a method of producing a plurality of modified polynucleotides from a parent polynucleotides that comprises the coding region of a subject protein, wherein each of the plurality modified polynucleotides encode a modified polypeptide that comprises an amino acid substitution at a first amino acid position of interest in the protein of interest. In some embodiments, the method comprises:

(a) providing a plurality of primers capable of binding to a desired region of the parent polynucleotides, wherein the desired region comprises the codon for the amino acid at the first position of interest of the subject protein, wherein at least N of the plurality of primers each comprise codon for a different alternative amino acid at the first amino acid position of interest, wherein N is the number of desired amino acid substitutions at the first position of interest;

(b) contacting the plurality of primers with the parent polynucleotide to form a reaction mixture; and (c) subjecting the reaction mixture to a polymerase-based reaction (PCR) to generate the plurality of modified polynucleotides.

In the methods disclosed herein, the plurality of primers can comprise primers each comprise a different codon for the same alternative amino acid. For example, for one alternative amino acid, two or more of different codons for the alternative amino acid can be present in the plurality of primers. In some embodiments, two or more different codons for one, two, three, four, or more of the alternative amino acids are present in the plurality of primers. In some embodiments, at least one of the plurality of primers comprises a second codon for one of the alternative amino acids. In some embodiments, the plurality of primers comprises at least two or more primers each comprising a second codon for a different alternative amino acid. As a non-limiting example, if serine (S) is at the first amino acid position of interest of a subject protein, alanine (A) is one of the alternative amino acids for substitution at this positon of interest. In some embodiments, the plurality of primers can comprise a primer comprising AUU, one of codons for alanine. In some embodiments, the plurality of primers can comprise a primer comprising AUU and another primer comprising AUC, another codon for alanine. In some embodiments, the plurality of primers can comprise a primer comprising AUU, a primer comprising AUC, and a primer comprising AUA, another codon for alanine. Depending on the number of desired amino acid substitutions at the amino acid position of interest, the value of N can be determined. If the amino acid substitutions are substitutions between standard amino acids (referred herein as "standard amino acid substitutions"), for any given position of interest, the maximum number for the amino acid substitutions is 19. Therefore, N is between 1 and 19. So that N can be, for example, 1, 2, 3, 4, 5, 6, 7, 8, 9, 10, 11, 12, 13, 14, 15, 16, 17, 18, 19, or a range between any two of these values. Depending on the value of N, the method can provide flexibility to exclude unwanted amino acid changes at specified sites. For example, if only a subset of the 12 standard amino acid changes (that is, not all possible 19 standard amino acid changes) are desired, a pool of 12 predetermined oligos can be used instead of 19. In some embodiments, the method is used for pre-selecting desired codons for maximizing protein expression. In some embodiments, codons can be differentially selected based on the known codon preferences for maximizing expression in the screening host.

In some embodiments, N is 19. That is, 19 different oligonucleotides (e.g., primers) are used to introduce amino acid changes to a given amino acid position in a subject protein, for example, the amino acid changes can include all possible changes from the amino acid in the subject protein to an alternative standard amino acid. For example, if one is to use GSSM 2.2 to modify a proline in a target position of a protein of interest, in some embodiments, 19 different oligonucleotides each comprising a codon for one of the non-proline standard amino acids (i.e., alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), serine (S), threonine (T), tryptophan (W), tyrosine (Y), and valine (V)) can be used to generate a set of 19 variants of the protein of interest. The set of 19 variants comprises variants having a complete set of all possible amino acid substitutions at the target position (i.e., substation from Proline to Alanine (referred herein as "P→A"), P→R, P→N, P→D, P→C, P→E, P→Q, P→G, P→HI, P→I, P→L, P→K, P→M, P→F, P→S, P→T, P→W, P→Y, and P→V.

In some embodiments, the plurality of polynucleotides produced by the improved GSSM method disclosed herein comprises polynucleotides that encode for polypeptides having all possible standard amino acid substitutions at the first amino acid position of interest as compared to the subject protein. In some embodiments, in the improved GSSM method disclosed herein, plurality of primers does not comprise degenerate primers.

The plurality of primers can be designed based on the sequence of the desired region of the parent polynucleotide. For example, in some embodiments, at least one of the plurality of primers is capable of binding to a region between 20 nucleotides upstream and 20 nucleotides downstream of the codon for the amino acid at the first amino acid position of interest. The GSSM 2.2 method can further comprise one or more of steps (1) treating the plurality of modified polynucleotides generated in step (c) with a restriction enzyme to remove the parent polynucleotide, (2) recovering the plurality of modified polynucleotides, or both, and (3) introducing one or more of the modified polynucleotides to a host cell to express one or more mutants of the subject protein.

The codon in the primers can be selected according to the need(s) of one of skill in the art. In some embodiments, at least one of the codons in the primers for the different alternative amino acids at the first amino acid position of interest is a preferred codon of the host cell. Various types of host cells can be used in the improved GSSM method disclosed herein. For example, the host cell can be a eukaryotic cell or a prokaryotic cell. In some embodiments, the host cell is a cell from an organism selected from the group consisting of *Pichia pastoris* (*Komagataella pastoris*), *Bacillus subtilis*, *Pseudomonas fluorescens*, *Myceliopthora thermophile* fungus, *Aspergillus niger*, *Tricodermea ressii*, and *Escherichia coli*.

The one or more mutants of the subject protein expressed by the modified polynucleotides can be analyzed, in some embodiments, for stability, thermostability, substrate specificity, activity, stereoselectivity, expression (e.g., expression level or expression pattern), pH profile change (e.g., change to higher or lower pH), co-factor specificity, product inhibition, salt tolerance, sensitivity to salt concentration, sensitivity to salt, binding affinity, or a combination thereof. In some embodiments, one or more mutants of the subject protein are selected based on their stability, thermostability, substrate specificity, activity, stereoselectivity, expression (e.g., expression level or expression pattern), pH profile change (e.g., change to higher or lower pH), co-factor specificity, product inhibition, salt tolerance, sensitivity to salt concentration, sensitivity to salt, binding affinity, or a combination thereof.

The form of the parent polynucleotide is not limited. For example, the parent polynucleotide is a double-stranded DNA or single stranded DNA. The parent polynucleotide can be linear or in circular form. In some embodiments, the parent polynucleotide is a circular double-stranded DNA.

The improved GSSM method disclosed herein can be used to introduce amino acid substitution(s) to one, two or more sites in a subject protein. For example, the method can be used to introduce amino acid substitution(s) to two different amino acid positions of the subject protein. In some embodiments, the plurality of primers comprises at least M additional primers each comprising codon for a different alternative amino acid at a second amino acid position of interest of the subject protein, wherein M is the number of desired amino acid substitutions at the second position of interest. In some embodiments, M is an integer between 1 and 19. In some embodiments, M is 19. In some embodiments, at least one of the plurality of modified polynucleotides encodes a polypeptide comprising an amino acid substitution at the second amino acid position of interest. In some embodiments, the plurality of polynucleotides comprises polynucleotides that encode for modified polypeptides having all possible standard amino acid substitutions at the second amino acid position of interest as compared to the subject protein. In some embodiments, at least one of the plurality of modified polynucleotides encodes a modified polypeptide comprising an amino acid substitution at the first and the second amino acid positions of interest, respectively. In some embodiments, the plurality of polynucleotides comprises polynucleotides that encode for modified polypeptides having all possible standard amino acid substitutions at the first amino acid positions of interest as compared to the subject protein as well as polynucleotides that encode for polypeptides having all possible standard amino acid substitutions at the second amino acid positions of interest as compared to the subject protein. In some embodiments, one or more modified polypeptides have substitution at both the first and the second positions. In some embodiments, one or more modified polypeptides only have substitution at one of the first and the second positions. As used herein, the first and the second amino acid positions of interest can be adjacent to each other, for example the first and second amino acid positions are contiguous on the polypeptide; however, in some other embodiments, the first and second amino acid positions of interest are not adjacent to each other. In addition, the order of the first and the second amino acid positions of interest can vary. For example, the first amino acid position of interest can be closer to the N-terminus of the polypeptide than the second amino acid position of interest. In some other embodiments, the first amino acid position of interest is closer to the C-terminus of the polypeptide than the second amino acid position of interest.

In some embodiments, the improved GSSM method disclosed herein (i.e., GSSM 2.2) can prevent biases towards certain amino acids. Earlier GSSM techniques using N, N, K, or N, N, N generates libraries with biases towards certain amino acid changes at each site. Statistically, the frequency of difference amino acids in the library at each site ranges from 2-9% for NNN, 3-9% for NNK. In some embodiments, assuming each oligo pool used in the reaction is equimolar, the frequency of each amino acid is 5.26%. In some embodiments, GSSM 2.2 reduces the number of library clones that need to be screened. In some embodiments, to achieve 95% probability of complete coverage of screening each amino acid change at one amino acid site, 175 NNK library variants need to be screened compared to only 120 GSSM 2.2 library variants. This is roughly a 30% reduction in screening over previous techniques. FIG. 1 shows a comparison of the number of clones that must be screened in order to achieve 95% to 100% probability of complete coverage of each amino acid change at one amino acid site.

Due to the reduced screening times, GSSM 2.2 can allow for much quicker screening. For example, some embodiments of previous GSSM methods may require the screening of 32 codons per mutation. Based on such a screen, a 384 well plate would allow the screening of 2 residues per plate at ~5-5.5× coverage. Thus, for a polypeptide of approximately 436 amino acids, screening would take approximately 12 weeks. In modified forms of earlier GSSM approaches, limiting screening to 3.5× coverage reduces the overall screening time to approximately 9 weeks but increases the risk of biased codon frequency. Further the lower oversampling rates may miss some amino acid substitutions.

In some embodiments, one residue is changed at a time to cover all 20 amino acids. The library is screened and up-mutants identified. These up-mutants can then be used to design polypeptides containing mutations at multiple sites of one molecule. For example, U.S. Pat. No. 9,476,078, which is incorporated herein by reference, describes a tailored multi-site combinatorial assembly (TMCA) reaction designed for making mutations at multiple sites of one molecule. The TMCA reaction can be used, in some embodiments to combine the up-mutants identified from the GSSM 2.2 library. Under the conditions of the TMCA reaction, one would expect formation of multiple PCR products.

Sources of the parent polynucleotides is not limited. For example, the parent polynucleotide can be isolated from individual organisms ("isolates"), collections of organisms that have been grown in defined media ("enrichment cultures"), or, most preferably, uncultivated organisms ("environmental samples"). The use of a culture-independent approach to derive polynucleotides encoding novel bioactivities from environmental samples is most preferable since it allows one to access untapped resources of biodiversity.

The organisms from which the parent polynucleotide may be prepared include, but are not limited to, prokaryotic microorganisms, such as Eubacteria and Archaebacteria; and lower eukaryotic microorganisms, such as fungi, some algae and protozoa. The prokaryotic microorganisms can be extremophiles, including but not limited to, hyperthermophiles, psychrophiles, psychrotrophs, halophiles, barophiles and acidophiles. The parent polynucleotides can also be isolated from environmental samples in which case the nucleic acid may be recovered without culturing of an organism or recovered from one or more cultured organisms.

Polynucleotides selected and isolated as hereinabove described are introduced into a suitable host cell. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al, 1986).

As representative examples of appropriate hosts, there may be mentioned: bacterial cells, such as *E. coli* and *Pseudomonas fluorescens*; bacteriophage; fungal cells, such as yeast, *Pichia pastoris* and *Aspergillus niger*; insect cells such as *Drosophila* S2 and *Spodoptera* Sf9; animal cells such as CHO, COS or Bowes melanoma; adenoviruses; and plant cells. The library can be made in, for example, in *E. coli* cells in the plasmid form, then the library can be further introduced into other hosts. The selection of an appropriate host is deemed to be within the scope of those skilled in the art from the teachings herein.

Different expression system, including but not limited to various mammalian cell culture systems, that can be employed to express recombinant protein, examples of mammalian expression systems include the COS-7 lines of monkey kidney fibroblasts, described in "SV40-transformed simian cells support the replication of early SV40 mutants" (Gluzman 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK (223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. In some embodiments, low copy number or high copy number vectors may be employed.

In some embodiments, a suitable vector contains an f-factor origin replication. The f-factor (or fertility factor) in *E. coli* is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

In some embodiments, a cosmid vector is used. Cosmid vectors were originally designed to clone and propagate large segments of genomic DNA. Cloning into cosmid vectors is described in detail in "Molecular Cloning: A laboratory Manual" (Sambrook et al, 1989).

The DNA sequence in the expression vector is operatively linked to an appropriate expression control sequence(s) (promoter) to direct RNA synthesis. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Generally, recombinant expression vectors will include origins of replication and selectable markers permitting transformation of the host cell, e.g., the ampicillin resistance gene of *E. coli* and *S. cerevisiae* TRP 1 gene, and a promoter derived from a highly-expressed gene to direct transcription of a downstream structural sequence. Such promoters can be derived from operons encoding glycolytic enzymes such as 3-phosphoglycerate kinase (PGK), .alpha.-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The DNA isolated or derived from microorganisms can preferably be inserted into a vector or a plasmid prior to probing for selected DNA. Such vectors or plasmids are preferably those containing expression regulatory sequences, including promoters, enhancers and the like. Such polynucleotides can be part of a vector and/or a composition and still be isolated, in that such vector or composition is not naturallyly occurring. Particularly preferred phage or plasmid and methods for introduction and packaging into them are described in detail in the protocol set forth herein.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

In some embodiments, a suitable number of unique primers, primer pairs or primer sets are designed and synthesized for each location of interest in a template polynucleotide. Preferably, the primers are designed to comprise a mutation at a location of interest. Even more preferably, a plurality of primers is designed to comprise more than one different mutation at a location of interest in a polynucleotide. In some embodiments, a suitable number of primers may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 60, 70, 80, 90, 100 or more primers. A primer pair or set comprises a combination of forward primers and reverse primers capable of annealing to a polynucleotide of interest. The polynucleotide or DNA sequence of interest may be referred to as "template DNA" or "template polynucleotide." Each primer set comprises at least one mutation as compared to the template polynucleotide. Preferably, the 19 primer sets comprise mutations coding for all 19 amino acid variants corresponding to a residue at a specific position in the template sequence of interest. The primer pairs are used to set up polymerase extension reactions under the conditions detailed in the Examples. Then, the finished reactions are verified by agarose gels to determine if the reactions are successful. In some embodiments, a restriction enzyme (e.g., Dpn1) can be added to the reactions to degrade the "template polynucleotide." In some embodiments, the template polynucleotide is from an *E. coli* host. In some embodiments, the template polynucleotide is methylated. In some embodiments, the restriction enzyme-treated reactions are transformed into *E. coli* cells to recover the DNAs with desired mutations. The transformants can be, for example, screened by sequencing or a suitable assay as desired.

The methods disclosed herein are not limited to one or a few sites. Higher or lower number of positions can be assembled by this method. The methods are also not limited to a single change at one position. Multiple primers can be designed to cover different changes at the same position, with a single change on each primer. *E. coli* has been used for the demonstration; however, other bacterial hosts would work for this method. The method of the invention can not only introduce point mutation, it can also make deletions or insertions or multiple mutations.

The reactions can be altered with different reaction conditions, primer concentrations, primer $T_m$ (annealing temperature to a template), DNA polymerase types, template concentrations, primer combinations, and different hosts to control how the changes at different sites are assembled.

Generally, methods are provided for producing a plurality of progeny polynucleotides having multiple mutations at a single location of interest, various combinations of mutations at multiple sites, or all possible mutations at all potential sites. The method can be performed in part by a combination of at least one or more of the following steps:

Disclosed herein includes obtaining sequence information of a polynucleotide of interest ("template polynucleotide"). For example, the sequence can be a wild type, mutated, or non-naturally occurring sequence. The sequence information can be of the complete polynucleotide or of partial regions of interest, such as a sequence encoding a site for binding, binding-specificity, catalysis, or substrate-specificity. The polynucleotide can comprise a sequence such as an open reading frame, a gene, a polypeptide-encoding sequence, or an enzyme-encoding sequence, with or without a signal or secretion sequence.

Identifying at least one location of interest along the sequence of the polynucleotide, such as mutations at 1, 2, 3, 4, 5, 6, 7, 8, 9, 10, 11, 12, 13, 14, 15, 16, 17, 18, 19, 20, 25, 30, 35, 40, or 50 or more positions. The mutations can be at the polynucleotide sequence level or mutations to the amino acid sequence encoded by the polynucleotide sequence, e.g., codons. The positions can be predetermined by absolute position or by the context of surrounding residues or homology. The sequences flanking the mutation positions on either side are preferably known. Each mutation position may contain two or more mutations, such as for different amino acids. Such mutations can be identified by using Gene Site Saturation Mutagenesis (GSSM), as described above, and in U.S. Pat. Nos. 6,171,820, 6,562,594, or 6,764,835.

Designing and providing primers comprising the mutations of interest relative to the template sequence. The primers may be synthetic oligonucleotides. The primers may be synthesized using any suitable method or obtained commercially. Preferably, a primer is provided for each mutation of interest. The mutations can be changes in one or more nucleotide or encoded amino acid sequences, insertions or deletions. Thus, a position having 19 mutations of interest can use 19 primers at that position. The primer can also be provided as a pool of primers so that the mutation of interest is the range of any nucleotide, or a subset of that range. For example, a pool of primers can be provided that favor mutations for aliphatic amino acid residues. Preferably, a pool of primers is provided that allows for every amino acid variant at a particular position. Even more preferably, the pool of primers is optimized for codon usage of the host cell or cell-free protein expression system.

In some embodiments, the primers can be prepared as forward or reverse primers (for example for introducing two or more mutations into the subject protein), preferably at least one forward primer and at least one reverse primer, and more preferably a relatively balanced number of each (e.g., 19 forward and 19 reverse). Preferably, the primers are complementary to at least 10, 11, 12, 13, 14, 15, 16, 17, 18, 19, 20, 21, 22, 23, 24, 25, 26, 27, 28, 29, or 30 or more upstream or downstream nucleotides adjacent to the location of interest. When mutations are positioned closely together, it can be convenient to use primers that contain mutations for more than one position or different combinations of mutations at multiple positions. The methods and compositions disclosed herein can be used to introduce 1, 2, 3, 4, 5, 6, 7, 8, 9, 10, or a range between any two of these values, mutations into the subject protein. In some embodiments, at least 1, 2, 3, 4, 5, 6, 7, 8, 9, or 10 mutations are introduced into the subject protein. In some embodiments, no more than 1, 2, 3, 4, 5, 6, 7, 8, 9, or 10 mutations are introduced into the subject protein.

Providing a polynucleotide containing the template polynucleotide. The polynucleotide is preferably circular, more preferably super-coiled, such as a plasmid or vector for cloning, sequencing or expression. The polynucleotide may be single-stranded ("ssDNA"), and preferably double-stranded ("dsDNA"). Although the GSSM method may subject the supercoiled ("Sc") dsDNA template to a heating step at 95° C. for 1 min, the template does not become ssDNA (see Levy, NAR, 28(12):e57 (i-vii) (2000), shows that heating sc dsDNA to 95° C. for 5 min does not produce ssDNA molecules and is reversible if the molecules are cooled after heating (pages ii-iii, FIG. 2)).

Adding the primers to the template polynucleotide in a reaction mixture under conditions that allow the primers to anneal to the polynucleotide. Preferably, the primers are added to the polynucleotide in a single reaction mixture, but can be added in multiple reactions according to an experimental design.

Performing a polymerase extension of the primers, preferably allowing the extension to proceed completely around a circular template molecule. The extension products (as defined herein, "progeny" or "modified extended polynucleotide") may be amplified by conventional means. The extension products may also be used as template polynucleotides for additional rounds of polymerase extension reactions.

The products may be analyzed for length, sequence, desired nucleic acid properties, or expressed as polynucleotides and/or polypeptides. Other analysis methods include in-situ hybridization, sequence screening or expression screening. The analysis can include one or more rounds of screening and selecting for a desired property.

The products can also be transformed into a cell or other expression system, such as a cell-free system. The cell-free system may contain enzymes related to DNA replication, repair, recombination, transcription, and/or for translation. Exemplary hosts include bacterial, yeast, plant and animal cells and cell lines, and include *E. coli, Pseudomonas fluorescens, Pichia pastoris* and *Aspergillus niger*. For example, XL1-Blue or Stb12 strains of *E. coli* can be used as hosts. When using *E. coli* with Dpn1 (which can be used to remove undesired template after reaction), the template DNA may be from a Dam+ *E. coli* host that can methylate the DNA. The cells can be used for expression of the progeny polynucleotides.

Polynucleotides or polypeptide expression products can be retrieved from the cells and analyzed for length, sequence, desired nucleic acid properties, or expressed as polypeptides. The analysis can include one or more rounds of screening and selecting for a desired property.

The methods disclosed herein can, in some embodiments, be used with the same or different primers (for example, in a multiplexing manner) under different reaction conditions to promote products having different combinations or numbers of mutations.

Method of Producing Modified Polypeptides

Also disclosed herein is a method of producing a plurality of modified polypeptides of a parent polypeptide, wherein each of the plurality of modified polypeptide comprises an amino acid substitution at a first amino acid position of interest. In some embodiments, the method comprises: providing a plurality of primers capable of binding to a desired region of a template polynucleotide encoding the parent polypeptide, wherein the desired region comprises the codon for the amino acid at the first amino acid position of interest in the parent polypeptide, wherein at least N of the plurality of primers each comprise codon for a different alternative amino acid for the amino acid at the first amino acid position of interest, wherein N is the number of desired amino acid substitutions at the first position of interest; contacting the plurality of primers with the template polynucleotide to form a reaction mixture; subjecting the reaction mixture to a polymerase-based reaction (PCR) to generate the plurality of modified polynucleotides; and introducing the modified polynucleotides to a recombinant expression system to produce the plurality of modified polypeptides.

As disclosed above, the value of N can be determined based on the number of desired amino acid substitutions at the amino acid position of interest. If the amino acid substitutions are substitutions between standard amino acids (referred herein as "standard amino acid substitutions"), for any given position of interest, N is between 1 and 19. N can be, for example, 1, 2, 3, 4, 5, 6, 7, 8, 9, 10, 11, 12, 13, 14, 15, 16, 17, 18, 19, or a range between any two of these values. In some embodiments, N is 19. That is, 19 different oligonucleotides (e.g., primers) are used to introduce amino acid changes to a given amino acid position in a subject protein, for example, the amino acid changes can include all possible changes from the amino acid in the subject protein to an alternative standard amino acid. In some embodiments, the plurality of primers does not comprise degenerate primers.

In some embodiments, the method comprises designing the plurality of primers based on the sequence of the desired region. In some embodiments, at least one of the plurality of primers is capable of binding to a region between 20 nucleotides upstream and 20 nucleotides downstream of the codon for the amino acid at the first amino acid position of interest.

Any recombinant expression system, including in vitro and in vivo expression systems can be used. In some embodiments, the recombinant expression system is a cell free system. In some embodiments, the recombinant expression system comprises a host cell, for example, a eukaryotic cell or a prokaryotic cell. In some embodiments, at least one of the codons in the primers for the different alternative amino acids at the first amino acid position of interest is a preferred codon of the host cell.

In some embodiments, the method further comprises analyzing one or more of the modified polypeptides for one or more desired properties, including but not limited to stability, thermostability, substrate specificity, activity, stereoselectivity, expression (e.g., expression level or expression pattern), pH profile change (e.g., change to higher or lower pH), co-factor specificity, product inhibition, salt tolerance, sensitivity to salt concentration, sensitivity to salt, binding affinity, or a combination thereof. The method, in some embodiments, further comprises selecting one or more mutants of the subject protein based on one or more desired properties of the mutant, including but not limited to, stability, thermostability, substrate specificity, activity, stereoselectivity, expression (e.g., expression level or expression patter), pH profile change (change to higher or lower pH), co-factor specificity, product inhibition, salt tolerance, sensitivity to salt concentration, sensitivity to salt, binding affinity, or a combination thereof. In some embodiments, the template polynucleotide is a circular double-stranded DNA.

Using the improved GSSM method disclosed herein, modified polypeptides with single, double, triple, or more combination of mutations can be obtained. In some embodiments, the plurality of primers comprises at least M additional primers each comprising codon for a different alternative amino acid at a second amino acid position of interest of the subject protein, wherein M is the number of desired amino acid substitutions at the second position of interest. As discussed above with respect to N, the value of M can be also determined based on the number of desired amino acid substitutions at the amino acid position of interest. In some embodiments, M is an integer between 1 and 19. In some embodiments, M is 19. In some embodiments, at least one of the plurality of modified polypeptides comprises an amino acid substitution at the second amino acid position of interest. In some embodiments, the plurality of modified polynucleotides have all possible standard amino acid substitutions at the second amino acid position of interest as compared to the parent polypeptide.

Also disclosed herein are methods for screening and/or selecting one or more polynucleotides produced by the GSSM method disclosed herein for one or more desired properties. One or more of the modified polynucleotides can be expressed for modified polypeptides, and optionally screened or selected for a desired property.

EXAMPLES

Some aspects of the embodiments discussed above are disclosed in further detail in the following examples, which are not in any way intended to limit the scope of the present disclosure.

Figure 3:
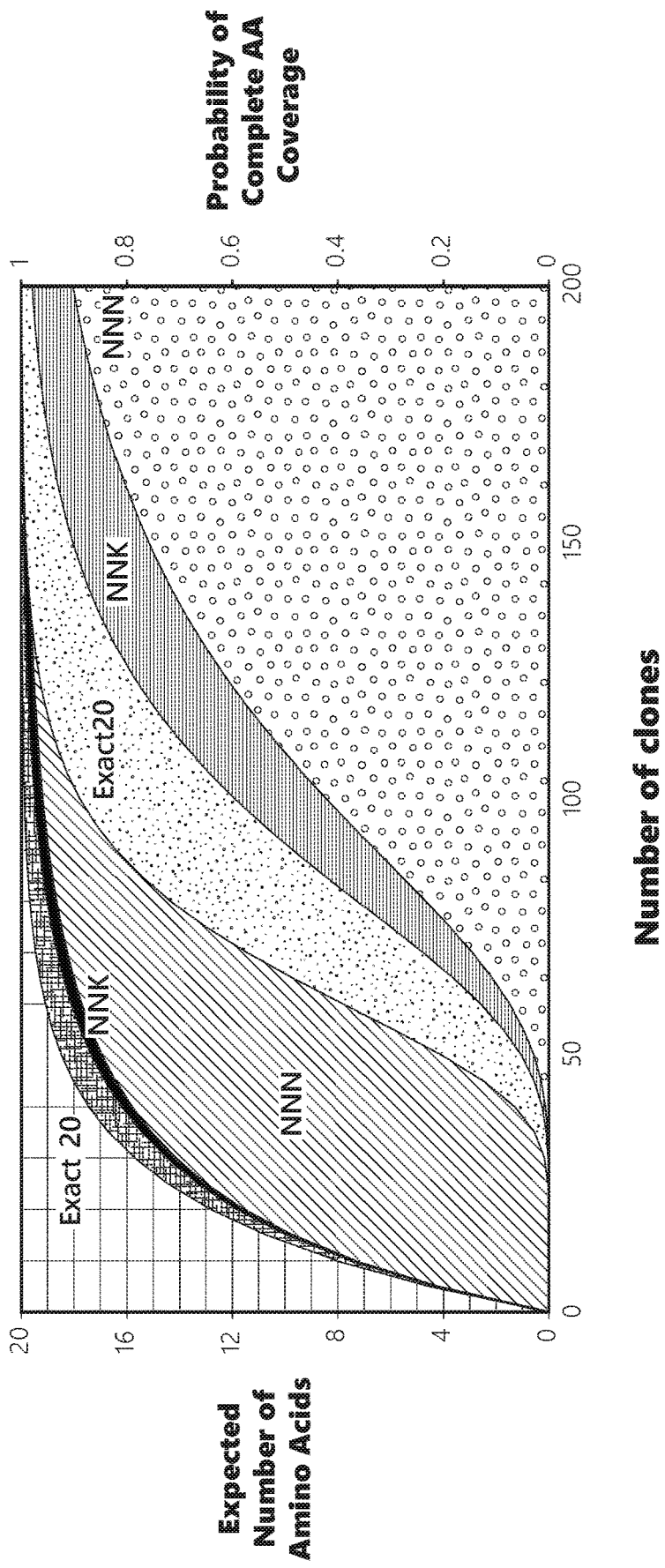
FIG. 3 is a graphical representation of the number of clones needed to approach 100% probability of complete amino acid coverage (all 20 amino acids) using different GSSM approaches.
Figure 4:
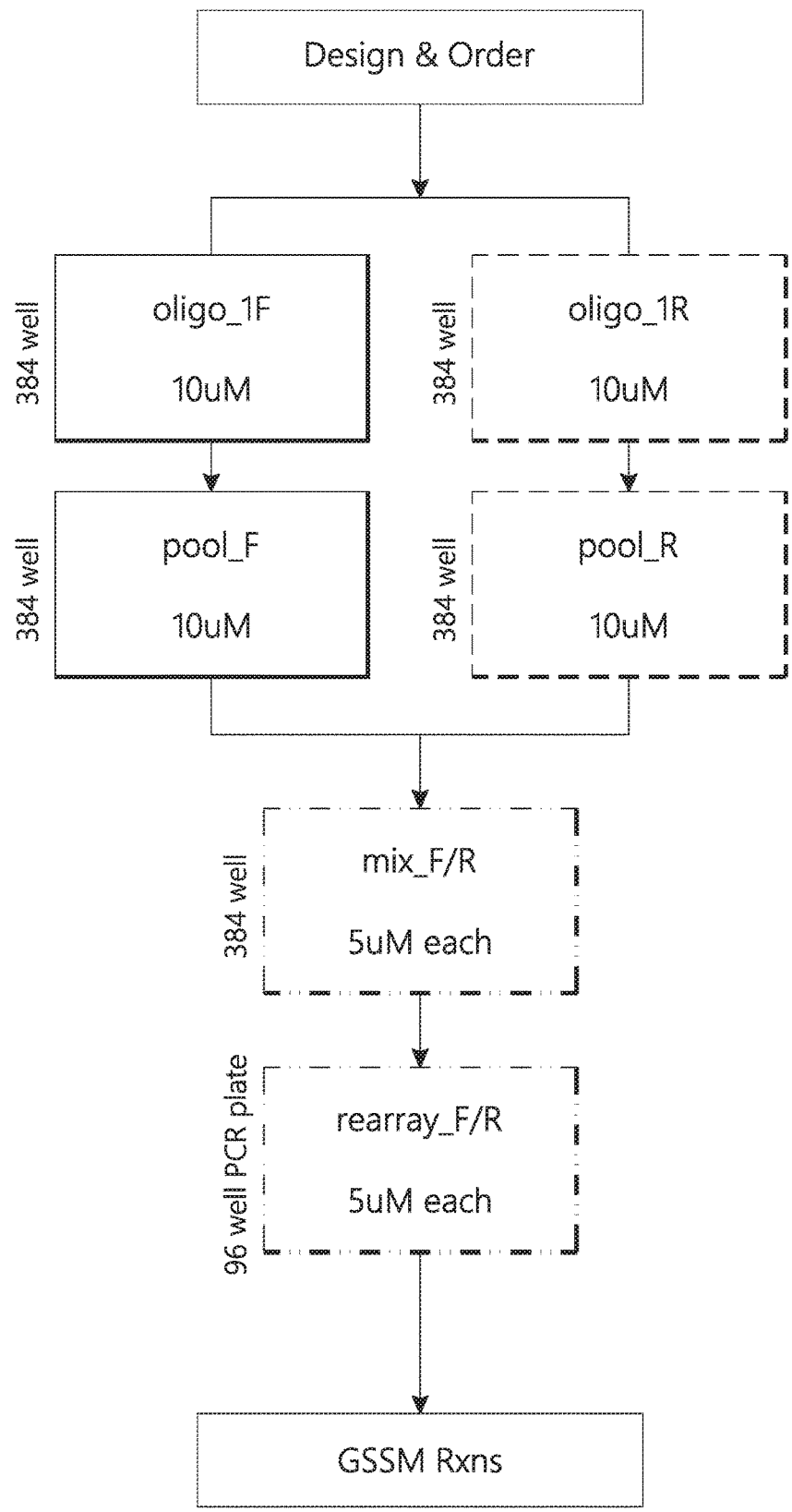
FIG. 4 is a schematic illustration of an exemplary primer design and preparation process for the GSSM method disclosed herein.

A protocol suitable for generating a whole or partial GSSM 2.2 library that can be screened for improved protein or polypeptide properties has been developed. Examples 1 to 3 are schematically illustrated in a workflow provided in FIG. 3.

Example 1

GSSM 2.2 Primer Design

A file of the gene of interest was created in a .FASTA format comprising the entire open reading frame (ORF) or region for mutagenesis with 20 bases of sequence before the first amino acid position to be mutated and 20 bases of sequences after the final amino acid position to be mutated.

Next, the .FASTA file was used to create oligos that serve as primers, both forward and reverse. A Codon Usage Chart file was created, specific to the host that the codons to be selected from, E. coli. 19 unique oligos were produced for each amino acid position of interest and each full 384-well plate contained oligos for at least 16 positions (for example, from rows A to P).

For example, a nuclease (nucleic acid sequence shown in SEQ ID NO: 1, and protein sequence shown in SEQ ID NO: 2) was selected as the gene of interest. 19 primers (forward or reverse primers) were designed for each of the amino acid positions of interest and to generate variants of the nuclease. The amino acid positions in the nuclease are shown in FIG. 1. Some exemplary primers designed for mutating a number of amino acids in the nuclease sequence are provided in Table 1, and the codons within the primer sequence to mutate the amino acid position of interest are in bold and underlined in Table 1.

TABLE 1

Primers

| Primer Name | Sequence (5'->3') | Primer Name | Sequence (5'->3') |
|---|---|---|---|
| For amino acid position 61 | | For amino acid position 62 | |
| 62_F_1 | GCAAGACTCGTAATTGGAAAGCGGA TCCAGCGTTGAATCCTGC (SEQ ID NO: 3) | 63_R_1 | TCAGCAGGATTCAACGCTGGCGCAGTTTT CCAATTACGAGTCT (SEQ ID NO: 22) |
| 62_F_2 | GCAAGACTCGTAATTGGAAATGCGA TCCAGCGTTGAATCCTGC (SEQ ID NO: 4) | 63_R_2 | TCAGCAGGATTCAACGCTGGGCAAGTTTT CCAATTACGAGTCT (SEQ ID NO: 23) |

TABLE 1-continued

Primers

| Primer Name | Sequence (5'->3') | Primer Name | Sequence (5'->3') |
|---|---|---|---|
| 62_F_3 | GCAAGACTCGTAATTGGAAAGATGATCCAGCGTTGAATCCTGC (SEQ ID NO: 5) | 63_R_3 | TCAGCAGGATTCAACGCTGGTTCAGTTTTCCAATTACGAGTCT (SEQ ID NO: 245) |
| 62_F_4 | GCAAGACTCGTAATTGGAAAGAAGATCCAGCGTTGAATCCTGC (SEQ ID NO: 6) | 63_R_4 | TCAGCAGGATTCAACGCTGGAAAAGTTTTCCAATTACGAGTCT (SEQ ID NO: 25) |
| 62_F_5 | GCAAGACTCGTAATTGGAAATTTGATCCAGCGTTGAATCCTGC (SEQ ID NO: 7) | 63_R_5 | TCAGCAGGATTCAACGCTGGGCCAGTTTTCCAATTACGAGTCT (SEQ ID NO: 26) |
| 62_F_6 | GCAAGACTCGTAATTGGAAAGGCGATCCAGCGTTGAATCCTGC (SEQ ID NO: 8) | 63_R_6 | TCAGCAGGATTCAACGCTGGATGAGTTTTCCAATTACGAGTCT (SEQ ID NO: 27) |
| 62_F_7 | GCAAGACTCGTAATTGGAAACATGATCCAGCGTTGAATCCTGC (SEQ ID NO: 9) | 63_R_7 | TCAGCAGGATTCAACGCTGGAATAGTTTTCCAATTACGAGTCT (SEQ ID NO: 28) |
| 62_F_8 | GCAAGACTCGTAATTGGAAAATTGATCCAGCGTTGAATCCTGC (SEQ ID NO: 10) | 63_R_8 | TCAGCAGGATTCAACGCTGGTTTAGTTTTCCAATTACGAGTCT (SEQ ID NO: 29) |
| 62_F_9 | GCAAGACTCGTAATTGGAAAAAAGATCCAGCGTTGAATCCTGC (SEQ ID NO: 11) | 63_R_9 | TCAGCAGGATTCAACGCTGGCAGAGTTTTCCAATTACGAGTCT (SEQ ID NO: 30) |
| 62_F_10 | GCAAGACTCGTAATTGGAAACTGGATCCAGCGTTGAATCCTGC (SEQ ID NO: 12) | 63_R_10 | TCAGCAGGATTCAACGCTGGCATAGTTTTCCAATTACGAGTCT (SEQ ID NO: 31) |
| 62_F_11 | GCAAGACTCGTAATTGGAAAATGGATCCAGCGTTGAATCCTGC (SEQ ID NO: 13) | 63_R_11 | TCAGCAGGATTCAACGCTGGGTTAGTTTTCCAATTACGAGTCT (SEQ ID NO: 32) |
| 62_F_12 | GCAAGACTCGTAATTGGAAAAACGATCCAGCGTTGAATCCTGC (SEQ ID NO: 14) | 63_R_12 | TCAGCAGGATTCAACGCTGGCGGAGTTTTCCAATTACGAGTCT (SEQ ID NO: 33) |
| 62_F_13 | GCAAGACTCGTAATTGGAAACCGGATCCAGCGTTGAATCCTGC (SEQ ID NO: 15) | 63_R_13 | TCAGCAGGATTCAACGCTGGCTGAGTTTTCCAATTACGAGTCT (SEQ ID NO: 34) |
| 62_F_14 | GCAAGACTCGTAATTGGAAACAGGATCCAGCGTTGAATCCTGC (SEQ ID NO: 16) | 63_R_14 | TCAGCAGGATTCAACGCTGGACGAGTTTTCCAATTACGAGTCT (SEQ ID NO: 35) |
| 62_F_15 | GCAAGACTCGTAATTGGAAACGTGATCCAGCGTTGAATCCTGC (SEQ ID NO: 17) | 63_R_15 | TCAGCAGGATTCAACGCTGGGCTAGTTTTCCAATTACGAGTCT (SEQ ID NO: 36) |
| 62_F_16 | GCAAGACTCGTAATTGGAAAAGCGATCCAGCGTTGAATCCTGC (SEQ ID NO: 18) | 63_R_16 | TCAGCAGGATTCAACGCTGGGGTAGTTTTCCAATTACGAGTCT (SEQ ID NO: 37) |
| 62_F_17 | GCAAGACTCGTAATTGGAAAGTGGATCCAGCGTTGAATCCTGC (SEQ ID NO: 19) | 63_R_17 | TCAGCAGGATTCAACGCTGGCACAGTTTTCCAATTACGAGTCT (SEQ ID NO: 38) |
| 62_F_18 | GCAAGACTCGTAATTGGAAATGGGATCCAGCGTTGAATCCTGC (SEQ ID NO: 20) | 63_R_18 | TCAGCAGGATTCAACGCTGGCCAAGTTTTCCAATTACGAGTCT (SEQ ID NO: 39) |
| 62_F_19 | GCAAGACTCGTAATTGGAAATATGATCCAGCGTTGAATCCTGC (SEQ ID NO: 21) | 63_R_19 | TCAGCAGGATTCAACGCTGGATAAGTTTTCCAATTACGAGTCT (SEQ ID NO: 40) |
| For amino acid position 85 | | For amino acid position 86 | |
| 86_F_1 | GCGCTAATGCCGCTCTTAAAGCGGATCGTGGGCACCAGGCGCC (SEQ ID NO: 41) | 87_R_1 | AGCGGCGCCTGGTGCCCACGCGCCACTTTAAGAGCGGCATTAG (SEQ ID NO: 60) |

TABLE 1-continued

Primers

| Primer Name | Sequence (5'->3') | Primer Name | Sequence (5'->3') |
|---|---|---|---|
| 86_F_2 | GCGCTAATGCCGCTCTTAAATGCGATCGTGGGCACCAGGCGCC (SEQ ID NO: 42) | 87_R_2 | AGCGGCGCCTGGTGCCCACGGCACACTTTAAGAGCGGCATTAG (SEQ ID NO: 61) |
| 86_F_3 | GCGCTAATGCCGCTCTTAAAGATGATCGTGGGCACCAGGCGCC (SEQ ID NO: 43) | 87_R_3 | AGCGGCGCCTGGTGCCCACGTTCCACTTTAAGAGCGGCATTAG (SEQ ID NO: 62) |
| 86_F_4 | GCGCTAATGCCGCTCTTAAAGAAGATCGTGGGCACCAGGCGCC (SEQ ID NO: 44) | 87_R_4 | AGCGGCGCCTGGTGCCCACGAAACACTTTAAGAGCGGCATTAG (SEQ ID NO: 63) |
| 86_F_5 | GCGCTAATGCCGCTCTTAAATTTGATCGTGGGCACCAGGCGCC (SEQ ID NO: 45) | 87_R_5 | AGCGGCGCCTGGTGCCCACGGCCCACTTTAAGAGCGGCATTAG (SEQ ID NO: 64) |
| 86_F_6 | GCGCTAATGCCGCTCTTAAAGGCGATCGTGGGCACCAGGCGCC (SEQ ID NO: 46) | 87_R_6 | AGCGGCGCCTGGTGCCCACGATGCACTTTAAGAGCGGCATTAG (SEQ ID NO: 65) |
| 86_F_7 | GCGCTAATGCCGCTCTTAAACATGATCGTGGGCACCAGGCGCC (SEQ ID NO: 47) | 87_R_7 | AGCGGCGCCTGGTGCCCACGAATCACTTTAAGAGCGGCATTAG (SEQ ID NO: 66) |
| 86_F_8 | GCGCTAATGCCGCTCTTAAAATTGATCGTGGGCACCAGGCGCC (SEQ ID NO: 48) | 87_R_8 | AGCGGCGCCTGGTGCCCACGTTTCACTTTAAGAGCGGCATTAG (SEQ ID NO: 67) |
| 86_F_9 | GCGCTAATGCCGCTCTTAAAAAAGATCGTGGGCACCAGGCGCC (SEQ ID NO: 49) | 87_R_9 | AGCGGCGCCTGGTGCCCACGCAGCACTTTAAGAGCGGCATTAG (SEQ ID NO: 68) |
| 86_F_10 | GCGCTAATGCCGCTCTTAAACTGGATCGTGGGCACCAGGCGCC (SEQ ID NO: 50) | 87_R_10 | AGCGGCGCCTGGTGCCCACGCATCACTTTAAGAGCGGCATTAG (SEQ ID NO: 69) |
| 86_F_11 | GCGCTAATGCCGCTCTTAAAATGGATCGTGGGCACCAGGCGCC (SEQ ID NO: 51) | 87_R_11 | AGCGGCGCCTGGTGCCCACGGTTCACTTTAAGAGCGGCATTAG (SEQ ID NO: 70) |
| 86_F_12 | GCGCTAATGCCGCTCTTAAAAACGATCGTGGGCACCAGGCGCC (SEQ ID NO: 52) | 87_R_12 | AGCGGCGCCTGGTGCCCACGCGGCACTTTAAGAGCGGCATTAG (SEQ ID NO: 71) |
| 86_F_13 | GCGCTAATGCCGCTCTTAAACCGGATCGTGGGCACCAGGCGCC (SEQ ID NO: 53) | 87_R_13 | AGCGGCGCCTGGTGCCCACGCTGCACTTTAAGAGCGGCATTAG (SEQ ID NO: 72) |
| 86_F_14 | GCGCTAATGCCGCTCTTAAACAGGATCGTGGGCACCAGGCGCC (SEQ ID NO: 54) | 87_R_14 | AGCGGCGCCTGGTGCCCACGACGCACTTTAAGAGCGGCATTAG (SEQ ID NO: 73) |
| 86_F_15 | GCGCTAATGCCGCTCTTAAACGTGATCGTGGGCACCAGGCGCC (SEQ ID NO: 55) | 87_R_15 | AGCGGCGCCTGGTGCCCACGGCTCACTTTAAGAGCGGCATTAG (SEQ ID NO: 74) |
| 86_F_16 | GCGCTAATGCCGCTCTTAAAAGCGATCGTGGGCACCAGGCGCC (SEQ ID NO: 56) | 87_R_16 | AGCGGCGCCTGGTGCCCACGGGTCACTTTAAGAGCGGCATTAG (SEQ ID NO: 75) |
| 86_F_17 | GCGCTAATGCCGCTCTTAAAACCGATCGTGGGCACCAGGCGCC (SEQ ID NO: 57) | 87_R_17 | AGCGGCGCCTGGTGCCCACGCACCACTTTAAGAGCGGCATTAG (SEQ ID NO: 76) |
| 86_F_18 | GCGCTAATGCCGCTCTTAAATGGGATCGTGGGCACCAGGCGCC (SEQ ID NO: 58) | 87_R_18 | AGCGGCGCCTGGTGCCCACGCCACACTTTAAGAGCGGCATTAG (SEQ ID NO: 77) |
| 86_F_19 | GCGCTAATGCCGCTCTTAAATATGATCGTGGGCACCAGGCGCC (SEQ ID NO: 59) | 87_R_19 | AGCGGCGCCTGGTGCCCACGATACACTTTAAGAGCGGCATTAG (SEQ ID NO: 78) |

TABLE 1-continued

Primers

| Primer Name | Sequence (5'->3') | Primer Name | Sequence (5'->3') |
|---|---|---|---|
| For amino acid position 87 | | For amino acid position 98 | |
| 98_F_1 | AGGCGCCGCTTGCGAGCCTGTGCGG TGTTTCAGACTGGGAAAG (SEQ ID NO: 79) | 99_R_1 | AGGCTTTCCCAGTCTGAAACCGCCGCCAG GCTCGCAAGCGGCG (SEQ ID NO: 98) |
| 98_F_2 | AGGCGCCGCTTGCGAGCCTGGATGG TGTTTCAGACTGGGAAAG (SEQ ID NO: 80) | 99_R_2 | AGGCTTTCCCAGTCTGAAACGCACGCCAG GCTCGCAAGCGGCG (SEQ ID NO: 99) |
| 98_F_3 | AGGCGCCGCTTGCGAGCCTGGAAGG TGTTTCAGACTGGGAAAG (SEQ ID NO: 81) | 99_R_3 | AGGCTTTCCCAGTCTGAAACATCCGCCAG GCTCGCAAGCGGCG (SEQ ID NO: 100) |
| 98_F_4 | AGGCGCCGCTTGCGAGCCTGTTTGG TGTTTCAGACTGGGAAAG (SEQ ID NO: 82) | 99_R_4 | AGGCTTTCCCAGTCTGAAACTTCCGCCAG GCTCGCAAGCGGCG (SEQ ID NO: 101) |
| 98_F_5 | AGGCGCCGCTTGCGAGCCTGGGCGG TGTTTCAGACTGGGAAAG (SEQ ID NO: 83) | 99_R_5 | AGGCTTTCCCAGTCTGAAACAAACGCCAG GCTCGCAAGCGGCG (SEQ ID NO: 102) |
| 98_F_6 | AGGCGCCGCTTGCGAGCCTGCATGG TGTTTCAGACTGGGAAAG (SEQ ID NO: 84) | 99_R_6 | AGGCTTTCCCAGTCTGAAACATGCGCCAG GCTCGCAAGCGGCG (SEQ ID NO: 103) |
| 98_F_7 | AGGCGCCGCTTGCGAGCCTGATTGG TGTTTCAGACTGGGAAAG (SEQ ID NO: 85) | 99_R_7 | AGGCTTTCCCAGTCTGAAACAATCGCCAG GCTCGCAAGCGGCG (SEQ ID NO: 104) |
| 98_F_8 | AGGCGCCGCTTGCGAGCCTGAAAGG TGTTTCAGACTGGGAAAG (SEQ ID NO: 86) | 99_R_8 | AGGCTTTCCCAGTCTGAAACTTTCGCCAG GCTCGCAAGCGGCG (SEQ ID NO: 105) |
| 98_F_9 | AGGCGCCGCTTGCGAGCCTGCTGGG TGTTTCAGACTGGGAAAG (SEQ ID NO: 87) | 99_R_9 | AGGCTTTCCCAGTCTGAAACCAGCGCCAG GCTCGCAAGCGGCG (SEQ ID NO: 106) |
| 98_F_10 | AGGCGCCGCTTGCGAGCCTGATGGG TGTTTCAGACTGGGAAAG (SEQ ID NO: 88) | 99_R_10 | AGGCTTTCCCAGTCTGAAACCATCGCCAG GCTCGCAAGCGGCG (SEQ ID NO: 107) |
| 98_F_11 | AGGCGCCGCTTGCGAGCCTGAACGG TGTTTCAGACTGGGAAAG (SEQ ID NO: 89) | 99_R_11 | AGGCTTTCCCAGTCTGAAACGTTCGCCAG GCTCGCAAGCGGCG (SEQ ID NO: 108) |
| 98_F_12 | AGGCGCCGCTTGCGAGCCTGCCGGG TGTTTCAGACTGGGAAAG (SEQ ID NO: 90) | 99_R_12 | AGGCTTTCCCAGTCTGAAACCGGCGCCAG GCTCGCAAGCGGCG (SEQ ID NO: 109) |
| 98_F_13 | AGGCGCCGCTTGCGAGCCTGCAGGG TGTTTCAGACTGGGAAAG (SEQ ID NO: 91) | 99_R_13 | AGGCTTTCCCAGTCTGAAACCTGCGCCAG GCTCGCAAGCGGCG (SEQ ID NO: 110) |
| 98_F_14 | AGGCGCCGCTTGCGAGCCTGCGTGG TGTTTCAGACTGGGAAAG (SEQ ID NO: 92) | 99_R_14 | AGGCTTTCCCAGTCTGAAACACGCGCCAG GCTCGCAAGCGGCG (SEQ ID NO: 111) |
| 98_F_15 | AGGCGCCGCTTGCGAGCCTGAGCGG TGTTTCAGACTGGGAAAG (SEQ ID NO: 93) | 99_R_15 | AGGCTTTCCCAGTCTGAAACGCTCGCCAG GCTCGCAAGCGGCG (SEQ ID NO: 112) |
| 98_F_16 | AGGCGCCGCTTGCGAGCCTGACCGG TGTTTCAGACTGGGAAAG (SEQ ID NO: 94) | 99_R_16 | AGGCTTTCCCAGTCTGAAACGGTCGCCAG GCTCGCAAGCGGCG (SEQ ID NO: 113) |
| 98_F_17 | AGGCGCCGCTTGCGAGCCTGGTGGG TGTTTCAGACTGGGAAAG (SEQ ID NO: 95) | 99_R_17 | AGGCTTTCCCAGTCTGAAACCACCGCCAG GCTCGCAAGCGGCG (SEQ ID NO: 114) |
| 98_F_18 | AGGCGCCGCTTGCGAGCCTGTGGGG TGTTTCAGACTGGGAAAG (SEQ ID NO: 96) | 99_R_18 | AGGCTTTCCCAGTCTGAAACCCACGCCAG GCTCGCAAGCGGCG (SEQ ID NO: 115) |

TABLE 1-continued

Primers

| Primer Name | Sequence (5'->3') | Primer Name | Sequence (5'->3') |
|---|---|---|---|
| 98_F_19 | AGGCGCCGCTTGCGAGCCTGTATGG TGTTTCAGACTGGGAAAG (SEQ ID NO: 97) | 99_R_19 | AGGCTTTCCCAGTCTGAAACATACGCCAG GCTCGCAAGCGGCG (SEQ ID NO: 116) |

Example 2

Oligo Pooling, Mixing, and Rearraying

Once the oligos were designed, they were synthesized by a commercially available source (Integrated DNA Technologies, Coralville, Iowa). The 25 nmole DNA oligos were stored in a 100 µl volume at a concentration of 10 µM in IDTE Buffer pH 8.0 (10 mM Tris-HCl, 0.1 mM EDTA) purified using standard desalting. The oligos were then added to 384 Axygen Deep Well plates with matcap seals on wet plates. Spot check OD was performed to verify that normalization was accurate.

Oligo plates were thawed and spun down briefly to concentrate liquid at the bottom of the wells. The matcap seals were removed and discarded. The forward pool (i.e., Pool_F) and reverse pool (i.e., Pool_R) plates were then mixed using automated equipment. The result of the mixing produced a single 384-well deep well plate, each well containing a mixture of the F pooled oligos and of the R pooled oligos specific for a GSSM 2.2 reaction. The 384 Oligo Mix plate was then re-arrayed into a 96 well PCR plate.

Example 3

Setting up GSSM Reactions

A Master Mix of reagents was prepared according to the tables below, adding the Accuprime Pfx last.
Reaction Components

| Pfx Buffer [10x] | 2.5 µl |
| Template [25 ng/µl] | 1.0 µl |
| Primermix [5 µM each F/R] | 3.0 µl |
| Accuprime Pfx | 0.4 µl |
| DMSO (optional) | 0.5 µl |
| dH₂O | to 25 µl total |

Master Mix (on Ice)

| Pfx Buffer [10x] | 2.5 µl | x (# reactions +4) |
| Template [25 ng/µl] | 1.0 µl | x (# reactions +4) |
| Accuprime Pfx | 0.4 µl | x (# reactions +4) |
| DMSO (optional) | 0.5 µl | x (# reactions +4) |
| dH₂O | 17.6 µl | x (# reactions +4) |

Following the combination of the Master Mix reagents, the master mix was vortexed thoroughly. 22 µl aliquots of the master mix were added into each well. 3 µl from the oligo mix plate were added to the side of each well, taking caution not to introduce air bubbles into the reaction mix. The PCR plate was tightly sealed and briefly centrifuged to collect contents at the bottom of each well.

Example 4

Polymerase Extension Reaction Conditions

GSSM 2.2 reactions were then performed according to the cycling conditions below. The extension time of 1 min/kb is based on total plasmid size.
Cycling Reaction Conditions

| Initial denaturation | 95° C.; 3 min | 1 Cycle |
| Denaturation | 95° C.; 1 min | 20 Cycles |
| Anneal | 55° C.; 45 sec | |
| Extend | 68° C.; 1 min/kb | |
| Polish | 68° C.; 10 min | 1 Cycle |
| Hold | 4° C.; forever | 1 Cycle |

Example 5

Confirm GSSM 2.2 Reactions on Gel

5 µl from each GSSM reaction was pipetted into 5 µl of prepared 2× BlueJuice DNA loading buffer. PCR plates containing 5 µl 2× loading buffer per well were prepared beforehand and stored at 4° C. The plates were then briefly centrifuged to mix DNA and loading buffer.

10 µl of samples were loaded onto 2×32 BioRad 1% agarose gels. The gels were then run at 100V for 30-45 minutes. The gels were then evaluated to determine whether bands were present and the approximate size of each band.

Example 6

DpnI Enzyme Digest

A Master Mix was prepared containing the following:
Master Mix

| dH2O | 3.5 µl | x (# reactions +5) |
| 10X NEB Buffer 4 | 0.5 µl | x (# reactions +5) |
| DpnI (20 U/µl) | 1.0 µl | x (# reactions +5) |

5 µl of the mastermix was added to each reaction and incubated at 37° C. for 4-5 hours. Plates were then stored at −20° C. until ready for transformation.

Example 7

Quality Control of Library

Approximately 5% of the GSSM 2.2 reactions were selected for transformations. 1 µl of each reaction was transformed in XL1-Blue Supercompetent Cells from Agilent Technologies (Santa Clara, CA). 48 single colonies resulting from each transformation were used to evaluate gene amplification via colony PCR. The amplification efficiency for each reaction was then checked via DNA gel. The amplified PCR products were then sequenced for the mutation region and each product was analyzed to determine whether a mutation had occurred and if a mutation was present, whether the mutation was a substitution, insertion, or deletion.

Example 8

Transfer Library into Screening Host, Growth and Protein Expression, Screening

1 µl of each reaction was transformed into XL1-Blue per the manufacturer's protocol and plated onto appropriate selective agar plates. Each reaction was transformed into a screening host. Following screening, the colonies were then selected, grown, and used for protein expression. Single colonies from transformation plates were inoculated in growth media. The colonies were grown and expressed to isolate proteins appropriate for the *E. coli* host and the appropriate screening method. Screening was then performed using appropriate assay methods. For example, when the protein of interest was an amylase, an appropriate amylase activity assay was performed. Nuclease variants generated using the primers disclosed in Example 1 were tested using appropriate nuclease activity assays. Some variants were also tested for temperature profiling and/or pH profiling, and a number of variants with desired properties were identified.

Example 9

Comparison Between GSSM (NNK) and GSSM 2.2

A comparison between GSSM (NNK) and GSSM 2.2 was analyzed via sequencing and recorded in Table 2 below. Each polymerase extension reaction was transformed into the *E. coli* XL1-Blue host strain. As each GSSM reaction targets 2 adjacent amino acid positions in the gene, 12 pairs of adjacent amino acid positions were sequenced and analyzed. Each amino acid position was analyzed for (1) the number of colonies that demonstrated a mutation at the targeted amino acid site and (2) the number of different amino acids achieved at the targeted amino acid site.

Results pertaining to GSSM (NNK) were labeled "NNK" in Table 2. Results pertaining to GSSM 2.2 were labeled "2.2" in Table 2. The NNK-Sequenced or 2.2-Sequenced label refers to the number of colonies sequenced per reaction. The NNK-Mutations or 2.2-Mutation label refers to the number of colonies that show a mutation at the targeted amino acid site. NNK-Diversity and 2.2-Diversity refer to the number of different amino acids achieved at the targeted site. AA Position refers to the position of the amino acid within the primary sequence of the amino acid. GSSM (NNK) represents 0.72× coverage, whereas GSSM 2.2 represents 2.5× coverage.

The data shown in Table 2 demonstrates that even after accounting for the larger numbers of colonies sequenced in GSSM 2.2 reactions, GSSM 2.2 provided a superior diversity mutation rate over GSSM (NNK) at nearly every one of the 12 adjacent amino acid pairs. This data demonstrates the advantage of GSSM 2.2 over GSSM NNK.

TABLE 2

Comparison between GSSM (NNK) and GSSM 2.2

|  | Rxn 1 | | Rxn 2 | | Rxn 3 | | Rxn 4 | | Rxn 5 | | Rxn 6 | |
|---|---|---|---|---|---|---|---|---|---|---|---|---|
| AA Position | 7 | 8 | 35 | 36 | 71 | 72 | 117 | 118 | 175 | 176 | 197 | 198 |
| NNK-Sequenced | 46 | | 42 | | 48 | | 48 | | 48 | | 48 | |
| NNK-Mutations | 6 | 6 | 10 | 14 | 16 | 13 | 12 | 24 | 14 | 18 | 21 | 9 |
| NNK-Diversity | 5 | 6 | 8 | 8 | 10 | 7 | 9 | 14 | 7 | 10 | 12 | 8 |
| 2.2-Sequenced | 96 | | 96 | | 96 | | 96 | | 96 | | 96 | |
| 2.2-Mutations | 25 | 46 | 39 | 39 | 40 | 34 | 28 | 27 | 45 | 41 | 45 | 27 |
| 2,2-Diversity | 15 | 15 | 18 | 13 | 19 | 17 | 13 | 15 | 15 | 15 | 18 | 15 |

|  | Rxn 7 | | Rxn 8 | | Rxn 9 | | Rxn 10 | | Rxn 11 | | Rxn 12 | |
|---|---|---|---|---|---|---|---|---|---|---|---|---|
| AA Position | 211 | 212 | 257 | 258 | 279 | 280 | 323 | 324 | 405 | 406 | 423 | 424 |
| NNK-Sequenced | 48 | | 48 | | 40 | | 45 | | 48 | | 48 | |
| NNK-Mutations | 9 | 13 | 13 | 16 | 7 | 12 | 12 | 16 | 12 | 16 | 18 | 5 |
| NNK-Diversity | 6 | 8 | 7 | 9 | 4 | 8 | 6 | 11 | 10 | 7 | 9 | 5 |
| 2.2-Sequenced | 96 | | 96 | | 96 | | 96 | | 96 | | 96 | |
| 2.2-Mutations | 29 | 21 | 38 | 24 | 22 | 45 | 28 | 48 | 45 | 22 | 39 | 28 |
| 2,2-Diversity | 16 | 14 | 17 | 14 | 14 | 15 | 13 | 18 | 15 | 14 | 14 | 16 |

Figure 5:
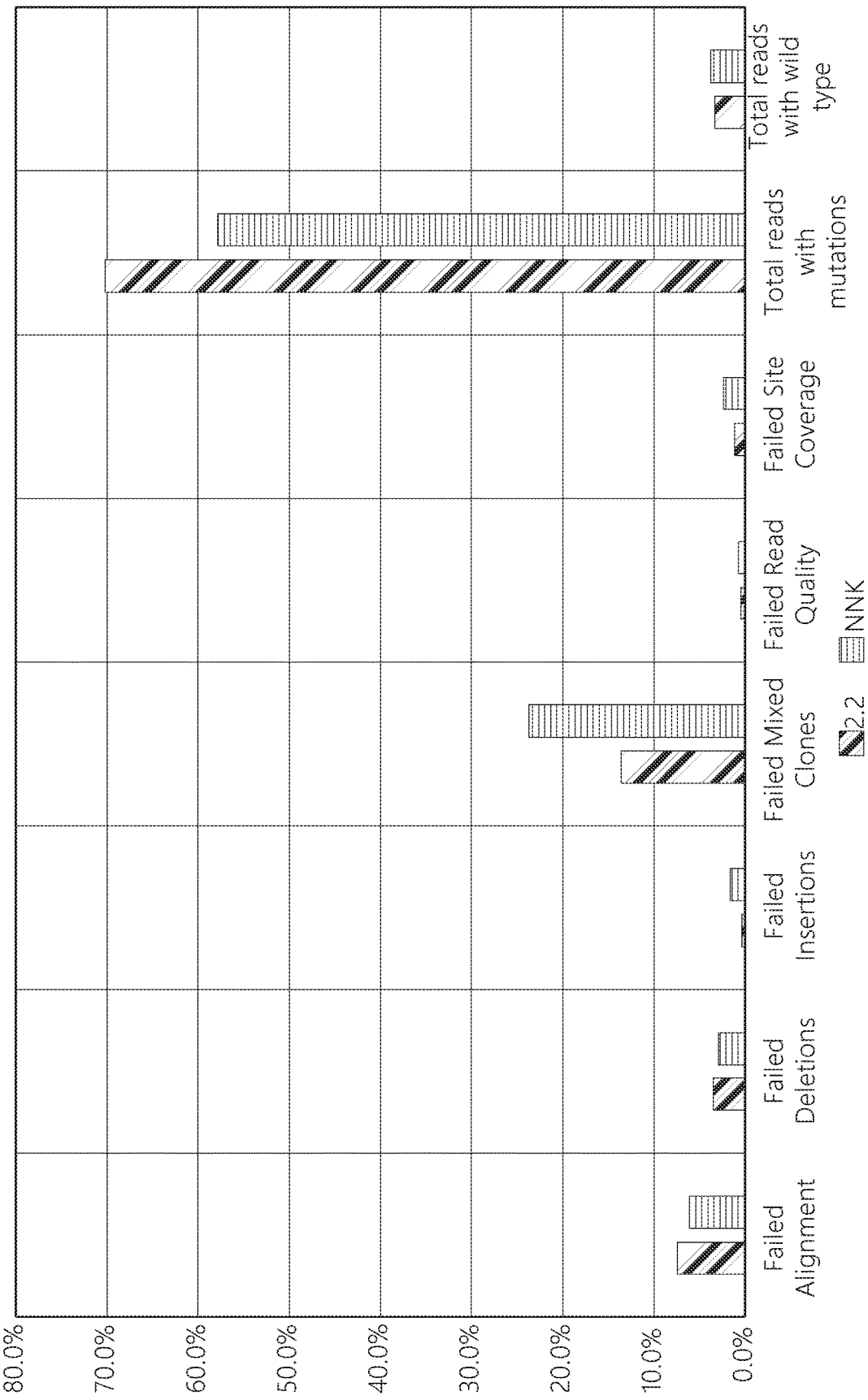
FIG. 5 is a graphical representation of experimental data comparing GSSM (NNK) to GSSM 2.2. The data demonstrates enhanced screening efficiency of GSSM 2.2 over GSSM (NNK).

An automated analysis was also performed on the GSSM (NNK) and GSSM 2.2 colonies based on the sequencing results for each colony sample to determine whether GSSM 2.2 produced a higher rate of unwanted insertion or deletion. Reads "Passed" included colony samples with both expected and off-site mutations and wildtypes. Reads "Failed" if one of the following occurred at each of the 12 selected adjacent amino acid sites: (1) the sample read failed an alignment, (2) the sample read comprised a deletion mutation, (3) the sample read comprised an insertion mutation, (4) the sample read was a mixed clone, (5) the sample failed read quality, or (6) the sample read failed site coverage. The mean results for all 12 selected adjacent amino acid sites (referenced as Reactions 1 to Reaction 12 in Table 2) are provided below in Table 3 and FIG. 5.

TABLE 3

Automated Analysis of GSSM 2.2 and GSSM (NNK)

|  | 2.2 | NNK |
|---|---|---|
| Reads Passed (%) | 73.5% | 62.4% |
| Reads Failed (%) | 26.4% | 37.6% |
| Failed Alignment | 7.4% | 5.8% |
| Failed Deletions | 3.5% | 2.9% |
| Failed Insertions | 0.3% | 1.6% |
| Failed Mixed Clones | 13.6% | 24.2% |
| Failed Read Quality | 0.4% | 0.7% |
| Failed Site Coverage | 1.1% | 2.3% |
| Total reads with mutations | 70.2% | 58.5% |
| Total reads with wild type | 3.3% | 3.9% |

The automated analysis of GSSM (NNK) and GSSM 2.2 facilitated a further evaluation of GSSM, namely whether the higher diversity rate of GSSM 2.2 in substitution mutations and higher overall substitution mutation rate was accompanied by mutations that would be detrimental to screening, such as through an increased production of unwanted deletion, insertion, or off-site mutations. A review of the automated analysis results in Chart 1 establishes that GSSM 2.2 does not meaningfully increase the rate of either deletion or insertion mutations as compared to GSSM (NNK). Noting that the automated analysis considered frame shift mutations (insertions/deletions) within the sequenced region of each clone, but did not reflect information concerning additional off-site amino acid substitution inducing mutations. Further, GSSM 2.2 demonstrated a lower failed alignment percentage than GSSM (NNK), establishing that the rate of off-site mutations was either lower or not statistically different than that of GSSM (NNK). Consequently, these results all affirm the superiority of GSSM 2.2 over GSSM (NNK) for screening efficiency.

The foregoing description and examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof. Although the present application has been described in detail above, it will be understood by one of ordinary skill in the art that various modifications can be made without departing from the spirit of the invention.

In the present application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein including, but not limited to, published and unpublished patent applications, patents, text books, literature references, and the like, to the extent that they are not already, are hereby incorporated by reference in their entirety. To the extent that one or more of the incorporated literature and similar materials differ from or contradict the disclosure contained in the specification, including but not limited to defined terms, term usage, described techniques, or the like, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method of producing a plurality of modified polynucleotides from a parent polynucleotide comprising the coding region of a subject protein, wherein each of the plurality of modified polynucleotides encode a modified polypeptide that comprises an amino acid substitution at a first amino acid position of interest in the protein of interest, the method comprising:
   (a) providing a plurality of primers capable of binding to a desired region of the parent polynucleotide, wherein the desired region comprises the codon for the amino acid at the first position of interest of the subject protein, wherein at least N of the plurality of primers each comprise a first codon for a different alternative amino acid at the first amino acid position of interest, wherein N is the number of desired amino acid substitutions at the first position of interest;
   (b) contacting the plurality of primers with the parent polynucleotide to form a reaction mixture; and
   (c) subjecting the reaction mixture to a polymerase extension reaction to generate the plurality of modified polynucleotides;
   wherein the plurality of primers does not comprise degenerate primers.

2. The method of claim 1, wherein at least one of the plurality of primers comprises a second codon for one of the alternative amino acids.

3. The method of claim 1, wherein the plurality of primers comprises at least two or more primers each comprising a second codon for a different alternative amino acid.

4. The method of claim 1, wherein N is an integer between 1 and 19.

5. The method of claim 1, wherein N is 19.

6. The method of claim 1, wherein the plurality of polynucleotides comprises polynucleotides that encode for polypeptides having all possible standard amino acid substitutions at the first amino acid position of interest as compared to the subject protein.

7. The method of claim 1, further comprising designing the plurality of primers based on the sequence of the desired region of the parent polynucleotide.

8. The method of claim 7, wherein at least one of the plurality of primers is capable of binding to a region between 20 nucleotides upstream and 20 nucleotides downstream of the codon for the amino acid at the first amino acid position of interest.

9. The method of claim 1, further comprising treating the plurality of modified polynucleotides generated in step (c) with a restriction enzyme to remove the parent polynucleotide.

10. The method of claim 1, further comprising recovering the plurality of modified polynucleotides.

11. The method of claim 1, further comprising introducing one or more of the modified polynucleotides to a host cell to express one or more mutants of the subject protein.

12. The method of claim 11, wherein at least one of the codons in the primers for the different alternative amino acids at the first amino acid position of interest is a preferred codon of the host cell.

13. The method of claim 11, further comprising analyzing the one or more mutants of the subject protein for stability, pH, product inhibition, salt tolerance, thermostability, substrate specificity, activity, stereoselectivity, expression, or a combination thereof.

14. The method of claim 13, further comprising selecting one or more mutants of the subject protein based on their stability, thermostability, substrate specificity, activity, stereoselectivity, expression, pH profile change (higher or lower pH), co-factor specificity, product inhibition, salt tolerance, sensitivity to salt concentration, sensitivity to salt, binding affinity, or a combination thereof.

15. The method of claim 11, wherein the host cell is a eukaryotic cell or a prokaryotic cell.

16. The method of claim 15, wherein the host cell is a cell from an organism selected from the group consisting of *Pichia pastoris, Bacillus licheniformis, Bacillus subtilis, Pseudomonas fluorescens, Myceliopthora thermophile* fungus, *Aspergillus niger, Trichoderma reesei*, and *Escherichia coli*.

17. The method of claim 1, wherein the parent polynucleotide is a circular double-stranded DNA.

18. The method of claim 1, wherein the plurality of primers comprises at least M additional primers each comprising codon for a different alternative amino acid at a second amino acid position of interest of the subject protein, wherein M is the number of desired amino acid substitutions at the second position of interest.

19. The method of claim 18, wherein M is an integer between 1 and 19.

20. The method of claim 18, wherein M is 19.

21. The method of claim 18, wherein at least one of the plurality of modified polynucleotides encodes a polypeptide comprising an amino acid substitution at the second amino acid position of interest.

22. The method of claim 18, wherein the plurality of polynucleotides comprises polynucleotides that encode for polypeptides having all possible standard amino acid substitutions at the second amino acid position of interest as compared to the subject protein.

23. A method of producing a plurality of modified polypeptides of a parent polypeptide comprising the coding region of a subject protein, wherein each of the plurality of modified polypeptides comprises an amino acid substitution at a first amino acid position of interest, the method comprising:
   providing a plurality of primers capable of binding to a desired region of a template polynucleotide encoding the parent polypeptide, wherein the desired region comprises the codon for the amino acid at the first amino acid position of interest in the parent polypeptide, wherein at least N of the plurality of primers each comprise a first codon for a different alternative amino acid for the amino acid at the first amino acid position of interest, wherein N is the number of desired amino acid substitutions at the first position of interest;
   contacting the plurality of primers with the template polynucleotide to form a reaction mixture;
   subjecting the reaction mixture to a polymerase extension reaction to generate the plurality of modified polynucleotides; and
   introducing the modified polynucleotides to a recombinant expression system to produce the plurality of modified polypeptides;
   wherein the plurality of primers does not comprise degenerate primers.

24. The method of claim 23, wherein at least one of the plurality of primers comprises a second codon for one of the alternative amino acids.

25. The method of claim 23, wherein the plurality of primers comprises at least two or more primers each comprising a second codon for a different alternative amino acid.

26. The method of claim 23, wherein N is an integer between 1 and 19.

27. The method of claim 23, wherein N is 19.

28. The method of claim 23, wherein the plurality of polynucleotides comprises polynucleotides that encode for polypeptides having all possible standard amino acid substitutions at the first amino acid position of interest as compared to the parent polypeptide.

29. The method of claim 23, further comprising designing the plurality of primers based on the sequence of the desired region.

30. The method of claim 23, wherein at least one of the plurality of primers is capable of binding to a region between 20 nucleotides upstream and 20 nucleotides downstream of the codon for the amino acid at the first amino acid position of interest.

31. The method of claim 23, wherein the recombinant expression system is a host cell.

32. The method of claim 31, wherein the host cell is a eukaryotic cell or a prokaryotic cell.

33. The method of claim 31, wherein at least one of the codons in the primers for the different alternative amino acids at the first amino acid position of interest is a preferred codon of the host cell.

34. The method of claim 31, wherein at least one of the codons in the primers for the different alternative amino acids at the first amino acid position of interest is the most preferred codon for an amino acid in the host cell.

35. The method of claim 23, further comprising analyzing one or more of the modified polypeptides for stability, thermostability, substrate specificity, activity, stereoselectivity, expression, pH profile change, co-factor specificity, product inhibition, salt tolerance, sensitivity to salt concentration, sensitivity to salt, binding affinity, or a combination thereof.

36. The method of claim 34, further comprising selecting one or more mutants of the subject protein based on their stability, thermostability, substrate specificity, activity, stereoselectivity, expression, pH profile change, co-factor specificity, product inhibition, salt tolerance, sensitivity to salt concentration, sensitivity to salt, binding affinity, or a combination thereof.

37. The method of claim 23, wherein the template polynucleotide is a circular double-stranded DNA.

38. The method of claim 23, wherein the plurality of primers comprises at least M additional primers each comprising codon for a different alternative amino acid at a second amino acid position of interest of the subject protein, wherein M is the number of desired amino acid substitutions at the second position of interest.

39. The method of claim 38, wherein M is an integer between 1 and 19.

40. The method of claim 38, wherein M is 19.

41. The method of claim 38, wherein at least one of the plurality of modified polypeptides comprises an amino acid substitution at the second amino acid position of interest.

42. The method of claim 38, wherein the plurality of modified polynucleotides have all possible standard amino acid substitutions at the second amino acid position of interest as compared to the parent polypeptide.

* * * * *

SEQUENCE LISTING

```
<160> NUMBER OF SEQ ID NOS: 116

<210> SEQ ID NO 1
<211> LENGTH: 735
<212> TYPE: DNA
<213> ORGANISM: Artificial Sequence
<220> FEATURE:
<223> OTHER INFORMATION: Nuclease

<400> SEQUENCE: 1
gatacactgg agagcattga caactgcgcc gtgggctgcc cgaccggcgg ttctagcaat      60
gttagtatcg tccgccatgc gtatactctg aataacaact ccaccaccaa atttgccaac     120
tgggtggcgt atcacattac taaagacaca cctgcgtcag gcaagactcg taattggaaa     180
actgatccag cgttgaatcc tgctgacacc ctggctccgg cggattatac cggcgctaat     240
gccgctctta aagtggatcg tgggcaccag gcgccgcttg cgagcctggc gggtgtttca     300
gactgggaaa gcctgaatta cctctcaaac atcacgccgc agaaaagtga tctgaatcaa     360
ggcgcgtggg cccgtctgga ggatcaggag cgcaaactta tcgatcgtgc agatattagt     420
agtgtgtata ctgtcacggg cccactgtac gaacgtgata tgggcaaact cccgggcacc     480
cagaaagctc acactattcc gtctgcgtac tggaaagtga tctttattaa caactccccg     540
gcggtgaatc attacgctgc gttttgttt gatcagaaca ccccaaaagg ggcggatttc     600
tgccagtttc gtgttaccgt tgatgaaatt gaaaaacgca caggcttaat tatctgggcg     660
ggcctgccaa atgacgtcca ggcgtccttg aaatccaagc cgggcgtgct gccggaactg     720
atgggttgca aaaac                                                      735

<210> SEQ ID NO 2
<211> LENGTH: 245
<212> TYPE: PRT
<213> ORGANISM: Artificial Sequence
```

```
<220> FEATURE:
<223> OTHER INFORMATION: Nuclease

<400> SEQUENCE: 2

Asp Thr Leu Glu Ser Ile Asp Asn Cys Ala Val Gly Cys Pro Thr Gly
1               5                   10                  15

Gly Ser Ser Asn Val Ser Ile Val Arg His Ala Tyr Thr Leu Asn Asn
            20                  25                  30

Asn Ser Thr Thr Lys Phe Ala Asn Trp Val Ala Tyr His Ile Thr Lys
        35                  40                  45

Asp Thr Pro Ala Ser Gly Lys Thr Arg Asn Trp Lys Thr Asp Pro Ala
    50                  55                  60

Leu Asn Pro Ala Asp Thr Leu Ala Pro Ala Asp Tyr Thr Gly Ala Asn
65                  70                  75                  80

Ala Ala Leu Lys Val Asp Arg Gly His Gln Ala Pro Leu Ala Ser Leu
                85                  90                  95

Ala Gly Val Ser Asp Trp Glu Ser Leu Asn Tyr Leu Ser Asn Ile Thr
            100                 105                 110

Pro Gln Lys Ser Asp Leu Asn Gln Gly Ala Trp Ala Arg Leu Glu Asp
        115                 120                 125

Gln Glu Arg Lys Leu Ile Asp Arg Ala Asp Ile Ser Ser Val Tyr Thr
    130                 135                 140

Val Thr Gly Pro Leu Tyr Glu Arg Asp Met Gly Lys Leu Pro Gly Thr
145                 150                 155                 160

Gln Lys Ala His Thr Ile Pro Ser Ala Tyr Trp Lys Val Ile Phe Ile
                165                 170                 175

Asn Asn Ser Pro Ala Val Asn His Tyr Ala Ala Phe Leu Phe Asp Gln
            180                 185                 190

Asn Thr Pro Lys Gly Ala Asp Phe Cys Gln Phe Arg Val Thr Val Asp
        195                 200                 205

Glu Ile Glu Lys Arg Thr Gly Leu Ile Ile Trp Ala Gly Leu Pro Asn
    210                 215                 220

Asp Val Gln Ala Ser Leu Lys Ser Lys Pro Gly Val Leu Pro Glu Leu
225                 230                 235                 240

Met Gly Cys Lys Asn
                245

<210> SEQ ID NO 3
<211> LENGTH: 43
<212> TYPE: DNA
<213> ORGANISM: Artificial Sequence
<220> FEATURE:
<223> OTHER INFORMATION: Primer

<400> SEQUENCE: 3
gcaagactcg taattggaaa gcggatccag cgttgaatcc tgc          43

<210> SEQ ID NO 4
<211> LENGTH: 43
<212> TYPE: DNA
<213> ORGANISM: Artificial Sequence
<220> FEATURE:
<223> OTHER INFORMATION: Primer

<400> SEQUENCE: 4
gcaagactcg taattggaaa tgcgatccag cgttgaatcc tgc          43

<210> SEQ ID NO 5
```

<211> LENGTH: 43
<212> TYPE: DNA
<213> ORGANISM: Artificial Sequence
<220> FEATURE:
<223> OTHER INFORMATION: Primer

<400> SEQUENCE: 5
gcaagactcg taattggaaa gatgatccag cgttgaatcc tgc        43

<210> SEQ ID NO 6
<211> LENGTH: 43
<212> TYPE: DNA
<213> ORGANISM: Artificial Sequence
<220> FEATURE:
<223> OTHER INFORMATION: Primer

<400> SEQUENCE: 6
gcaagactcg taattggaaa gaagatccag cgttgaatcc tgc        43

<210> SEQ ID NO 7
<211> LENGTH: 43
<212> TYPE: DNA
<213> ORGANISM: Artificial Sequence
<220> FEATURE:
<223> OTHER INFORMATION: Primer

<400> SEQUENCE: 7
gcaagactcg taattggaaa tttgatccag cgttgaatcc tgc        43

<210> SEQ ID NO 8
<211> LENGTH: 43
<212> TYPE: DNA
<213> ORGANISM: Artificial Sequence
<220> FEATURE:
<223> OTHER INFORMATION: Primer

<400> SEQUENCE: 8
gcaagactcg taattggaaa ggcgatccag cgttgaatcc tgc        43

<210> SEQ ID NO 9
<211> LENGTH: 43
<212> TYPE: DNA
<213> ORGANISM: Artificial Sequence
<220> FEATURE:
<223> OTHER INFORMATION: Primer

<400> SEQUENCE: 9
gcaagactcg taattggaaa catgatccag cgttgaatcc tgc        43

<210> SEQ ID NO 10
<211> LENGTH: 43
<212> TYPE: DNA
<213> ORGANISM: Artificial Sequence
<220> FEATURE:
<223> OTHER INFORMATION: Primer

<400> SEQUENCE: 10
gcaagactcg taattggaaa attgatccag cgttgaatcc tgc        43

<210> SEQ ID NO 11
<211> LENGTH: 43
<212> TYPE: DNA
<213> ORGANISM: Artificial Sequence
<220> FEATURE:
<223> OTHER INFORMATION: Primer

<400> SEQUENCE: 11
gcaagactcg taattggaaa aaagatccag cgttgaatcc tgc                            43

<210> SEQ ID NO 12
<211> LENGTH: 43
<212> TYPE: DNA
<213> ORGANISM: Artificial Sequence
<220> FEATURE:
<223> OTHER INFORMATION: Primer

<400> SEQUENCE: 12
gcaagactcg taattggaaa ctggatccag cgttgaatcc tgc                            43

<210> SEQ ID NO 13
<211> LENGTH: 43
<212> TYPE: DNA
<213> ORGANISM: Artificial Sequence
<220> FEATURE:
<223> OTHER INFORMATION: Primer

<400> SEQUENCE: 13
gcaagactcg taattggaaa atggatccag cgttgaatcc tgc                            43

<210> SEQ ID NO 14
<211> LENGTH: 43
<212> TYPE: DNA
<213> ORGANISM: Artificial Sequence
<220> FEATURE:
<223> OTHER INFORMATION: Primer

<400> SEQUENCE: 14
gcaagactcg taattggaaa aacgatccag cgttgaatcc tgc                            43

<210> SEQ ID NO 15
<211> LENGTH: 43
<212> TYPE: DNA
<213> ORGANISM: Artificial Sequence
<220> FEATURE:
<223> OTHER INFORMATION: Primer

<400> SEQUENCE: 15
gcaagactcg taattggaaa ccggatccag cgttgaatcc tgc                            43

<210> SEQ ID NO 16
<211> LENGTH: 43
<212> TYPE: DNA
<213> ORGANISM: Artificial Sequence
<220> FEATURE:
<223> OTHER INFORMATION: Primer

<400> SEQUENCE: 16
gcaagactcg taattggaaa caggatccag cgttgaatcc tgc                            43

<210> SEQ ID NO 17
<211> LENGTH: 43
<212> TYPE: DNA
<213> ORGANISM: Artificial Sequence
<220> FEATURE:
<223> OTHER INFORMATION: Primer

<400> SEQUENCE: 17
gcaagactcg taattggaaa cgtgatccag cgttgaatcc tgc                            43

<210> SEQ ID NO 18
<211> LENGTH: 43
<212> TYPE: DNA

<213> ORGANISM: Artificial Sequence
<220> FEATURE:
<223> OTHER INFORMATION: Primer

<400> SEQUENCE: 18
gcaagactcg taattggaaa agcgatccag cgttgaatcc tgc         43

<210> SEQ ID NO 19
<211> LENGTH: 43
<212> TYPE: DNA
<213> ORGANISM: Artificial Sequence
<220> FEATURE:
<223> OTHER INFORMATION: Primer

<400> SEQUENCE: 19
gcaagactcg taattggaaa gtggatccag cgttgaatcc tgc         43

<210> SEQ ID NO 20
<211> LENGTH: 43
<212> TYPE: DNA
<213> ORGANISM: Artificial Sequence
<220> FEATURE:
<223> OTHER INFORMATION: Primer

<400> SEQUENCE: 20
gcaagactcg taattggaaa tgggatccag cgttgaatcc tgc         43

<210> SEQ ID NO 21
<211> LENGTH: 43
<212> TYPE: DNA
<213> ORGANISM: Artificial Sequence
<220> FEATURE:
<223> OTHER INFORMATION: Primer

<400> SEQUENCE: 21
gcaagactcg taattggaaa tatgatccag cgttgaatcc tgc         43

<210> SEQ ID NO 22
<211> LENGTH: 43
<212> TYPE: DNA
<213> ORGANISM: Artificial Sequence
<220> FEATURE:
<223> OTHER INFORMATION: Primer

<400> SEQUENCE: 22
tcagcaggat tcaacgctgg cgcagttttc caattacgag tct         43

<210> SEQ ID NO 23
<211> LENGTH: 43
<212> TYPE: DNA
<213> ORGANISM: Artificial Sequence
<220> FEATURE:
<223> OTHER INFORMATION: Primer

<400> SEQUENCE: 23
tcagcaggat tcaacgctgg gcaagttttc caattacgag tct         43

<210> SEQ ID NO 24
<211> LENGTH: 43
<212> TYPE: DNA
<213> ORGANISM: Artificial Sequence
<220> FEATURE:
<223> OTHER INFORMATION: Primer

<400> SEQUENCE: 24
tcagcaggat tcaacgctgg ttcagttttc caattacgag tct         43

-continued

```
<210> SEQ ID NO 25
<211> LENGTH: 43
<212> TYPE: DNA
<213> ORGANISM: Artificial Sequence
<220> FEATURE:
<223> OTHER INFORMATION: Primer

<400> SEQUENCE: 25
tcagcaggat tcaacgctgg aaaagttttc caattacgag tct                43

<210> SEQ ID NO 26
<211> LENGTH: 43
<212> TYPE: DNA
<213> ORGANISM: Artificial Sequence
<220> FEATURE:
<223> OTHER INFORMATION: Primer

<400> SEQUENCE: 26
tcagcaggat tcaacgctgg gccagttttc caattacgag tct                43

<210> SEQ ID NO 27
<211> LENGTH: 43
<212> TYPE: DNA
<213> ORGANISM: Artificial Sequence
<220> FEATURE:
<223> OTHER INFORMATION: Primer

<400> SEQUENCE: 27
tcagcaggat tcaacgctgg atgagttttc caattacgag tct                43

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
tcagcaggat tcaacgctgg aatagttttc caattacgag tct                43

<210> SEQ ID NO 29
<211> LENGTH: 43
<212> TYPE: DNA
<213> ORGANISM: Artificial Sequence
<220> FEATURE:
<223> OTHER INFORMATION: Primer

<400> SEQUENCE: 29
tcagcaggat tcaacgctgg tttagttttc caattacgag tct                43

<210> SEQ ID NO 30
<211> LENGTH: 43
<212> TYPE: DNA
<213> ORGANISM: Artificial Sequence
<220> FEATURE:
<223> OTHER INFORMATION: Primer

<400> SEQUENCE: 30
tcagcaggat tcaacgctgg cagagttttc caattacgag tct                43

<210> SEQ ID NO 31
<211> LENGTH: 43
<212> TYPE: DNA
<213> ORGANISM: Artificial Sequence
<220> FEATURE:
```

<223> OTHER INFORMATION: Primer

<400> SEQUENCE: 31
tcagcaggat tcaacgctgg catagttttc caattacgag tct                43

<210> SEQ ID NO 32
<211> LENGTH: 43
<212> TYPE: DNA
<213> ORGANISM: Artificial Sequence
<220> FEATURE:
<223> OTHER INFORMATION: Primer

<400> SEQUENCE: 32
tcagcaggat tcaacgctgg gttagttttc caattacgag tct                43

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
tcagcaggat tcaacgctgg cggagttttc caattacgag tct                43

<210> SEQ ID NO 34
<211> LENGTH: 43
<212> TYPE: DNA
<213> ORGANISM: Artificial Sequence
<220> FEATURE:
<223> OTHER INFORMATION: Primer

<400> SEQUENCE: 34
tcagcaggat tcaacgctgg ctgagttttc caattacgag tct                43

<210> SEQ ID NO 35
<211> LENGTH: 43
<212> TYPE: DNA
<213> ORGANISM: Artificial Sequence
<220> FEATURE:
<223> OTHER INFORMATION: Primer

<400> SEQUENCE: 35
tcagcaggat tcaacgctgg acgagttttc caattacgag tct                43

<210> SEQ ID NO 36
<211> LENGTH: 43
<212> TYPE: DNA
<213> ORGANISM: Artificial Sequence
<220> FEATURE:
<223> OTHER INFORMATION: Primer

<400> SEQUENCE: 36
tcagcaggat tcaacgctgg gctagttttc caattacgag tct                43

<210> SEQ ID NO 37
<211> LENGTH: 43
<212> TYPE: DNA
<213> ORGANISM: Artificial Sequence
<220> FEATURE:
<223> OTHER INFORMATION: Primer

<400> SEQUENCE: 37
tcagcaggat tcaacgctgg ggtagttttc caattacgag tct                43

```
<210> SEQ ID NO 38
<211> LENGTH: 43
<212> TYPE: DNA
<213> ORGANISM: Artificial Sequence
<220> FEATURE:
<223> OTHER INFORMATION: Primer

<400> SEQUENCE: 38
tcagcaggat tcaacgctgg cacagttttc caattacgag tct            43

<210> SEQ ID NO 39
<211> LENGTH: 43
<212> TYPE: DNA
<213> ORGANISM: Artificial Sequence
<220> FEATURE:
<223> OTHER INFORMATION: Primer

<400> SEQUENCE: 39
tcagcaggat tcaacgctgg ccaagttttc caattacgag tct            43

<210> SEQ ID NO 40
<211> LENGTH: 43
<212> TYPE: DNA
<213> ORGANISM: Artificial Sequence
<220> FEATURE:
<223> OTHER INFORMATION: Primer

<400> SEQUENCE: 40
tcagcaggat tcaacgctgg ataagttttc caattacgag tct            43

<210> SEQ ID NO 41
<211> LENGTH: 43
<212> TYPE: DNA
<213> ORGANISM: Artificial Sequence
<220> FEATURE:
<223> OTHER INFORMATION: Primer

<400> SEQUENCE: 41
gcgctaatgc cgctcttaaa gcggatcgtg ggcaccaggc gcc            43

<210> SEQ ID NO 42
<211> LENGTH: 43
<212> TYPE: DNA
<213> ORGANISM: Artificial Sequence
<220> FEATURE:
<223> OTHER INFORMATION: Primer

<400> SEQUENCE: 42
gcgctaatgc cgctcttaaa tgcgatcgtg ggcaccaggc gcc            43

<210> SEQ ID NO 43
<211> LENGTH: 43
<212> TYPE: DNA
<213> ORGANISM: Artificial Sequence
<220> FEATURE:
<223> OTHER INFORMATION: Primer

<400> SEQUENCE: 43
gcgctaatgc cgctcttaaa gatgatcgtg ggcaccaggc gcc            43

<210> SEQ ID NO 44
<211> LENGTH: 43
<212> TYPE: DNA
<213> ORGANISM: Artificial Sequence
<220> FEATURE:
<223> OTHER INFORMATION: Primer
```

<400> SEQUENCE: 44
gcgctaatgc cgctcttaaa gaagatcgtg ggcaccaggc gcc    43

<210> SEQ ID NO 45
<211> LENGTH: 43
<212> TYPE: DNA
<213> ORGANISM: Artificial Sequence
<220> FEATURE:
<223> OTHER INFORMATION: Primer

<400> SEQUENCE: 45
gcgctaatgc cgctcttaaa tttgatcgtg ggcaccaggc gcc    43

<210> SEQ ID NO 46
<211> LENGTH: 43
<212> TYPE: DNA
<213> ORGANISM: Artificial Sequence
<220> FEATURE:
<223> OTHER INFORMATION: Primer

<400> SEQUENCE: 46
gcgctaatgc cgctcttaaa ggcgatcgtg ggcaccaggc gcc    43

<210> SEQ ID NO 47
<211> LENGTH: 43
<212> TYPE: DNA
<213> ORGANISM: Artificial Sequence
<220> FEATURE:
<223> OTHER INFORMATION: Primer

<400> SEQUENCE: 47
gcgctaatgc cgctcttaaa catgatcgtg ggcaccaggc gcc    43

<210> SEQ ID NO 48
<211> LENGTH: 43
<212> TYPE: DNA
<213> ORGANISM: Artificial Sequence
<220> FEATURE:
<223> OTHER INFORMATION: Primer

<400> SEQUENCE: 48
gcgctaatgc cgctcttaaa attgatcgtg ggcaccaggc gcc    43

<210> SEQ ID NO 49
<211> LENGTH: 43
<212> TYPE: DNA
<213> ORGANISM: Artificial Sequence
<220> FEATURE:
<223> OTHER INFORMATION: Primer

<400> SEQUENCE: 49
gcgctaatgc cgctcttaaa aaagatcgtg ggcaccaggc gcc    43

<210> SEQ ID NO 50
<211> LENGTH: 43
<212> TYPE: DNA
<213> ORGANISM: Artificial Sequence
<220> FEATURE:
<223> OTHER INFORMATION: Primer

<400> SEQUENCE: 50
gcgctaatgc cgctcttaaa ctggatcgtg ggcaccaggc gcc    43

<210> SEQ ID NO 51
<211> LENGTH: 43

```
<212> TYPE: DNA
<213> ORGANISM: Artificial Sequence
<220> FEATURE:
<223> OTHER INFORMATION: Primer

<400> SEQUENCE: 51
gcgctaatgc cgctcttaaa atggatcgtg ggcaccaggc gcc                    43

<210> SEQ ID NO 52
<211> LENGTH: 43
<212> TYPE: DNA
<213> ORGANISM: Artificial Sequence
<220> FEATURE:
<223> OTHER INFORMATION: Primer

<400> SEQUENCE: 52
gcgctaatgc cgctcttaaa aacgatcgtg ggcaccaggc gcc                    43

<210> SEQ ID NO 53
<211> LENGTH: 43
<212> TYPE: DNA
<213> ORGANISM: Artificial Sequence
<220> FEATURE:
<223> OTHER INFORMATION: Primer

<400> SEQUENCE: 53
gcgctaatgc cgctcttaaa ccggatcgtg ggcaccaggc gcc                    43

<210> SEQ ID NO 54
<211> LENGTH: 43
<212> TYPE: DNA
<213> ORGANISM: Artificial Sequence
<220> FEATURE:
<223> OTHER INFORMATION: Primer

<400> SEQUENCE: 54
gcgctaatgc cgctcttaaa caggatcgtg ggcaccaggc gcc                    43

<210> SEQ ID NO 55
<211> LENGTH: 43
<212> TYPE: DNA
<213> ORGANISM: Artificial Sequence
<220> FEATURE:
<223> OTHER INFORMATION: Primer

<400> SEQUENCE: 55
gcgctaatgc cgctcttaaa cgtgatcgtg ggcaccaggc gcc                    43

<210> SEQ ID NO 56
<211> LENGTH: 43
<212> TYPE: DNA
<213> ORGANISM: Artificial Sequence
<220> FEATURE:
<223> OTHER INFORMATION: Primer

<400> SEQUENCE: 56
gcgctaatgc cgctcttaaa agcgatcgtg ggcaccaggc gcc                    43

<210> SEQ ID NO 57
<211> LENGTH: 43
<212> TYPE: DNA
<213> ORGANISM: Artificial Sequence
<220> FEATURE:
<223> OTHER INFORMATION: Primer

<400> SEQUENCE: 57
```
gcgctaatgc cgctcttaaa accgatcgtg ggcaccaggc gcc    43

<210> SEQ ID NO 58
<211> LENGTH: 43
<212> TYPE: DNA
<213> ORGANISM: Artificial Sequence
<220> FEATURE:
<223> OTHER INFORMATION: Primer

<400> SEQUENCE: 58
gcgctaatgc cgctcttaaa tgggatcgtg ggcaccaggc gcc    43

<210> SEQ ID NO 59
<211> LENGTH: 43
<212> TYPE: DNA
<213> ORGANISM: Artificial Sequence
<220> FEATURE:
<223> OTHER INFORMATION: Primer

<400> SEQUENCE: 59
gcgctaatgc cgctcttaaa tatgatcgtg ggcaccaggc gcc    43

<210> SEQ ID NO 60
<211> LENGTH: 43
<212> TYPE: DNA
<213> ORGANISM: Artificial Sequence
<220> FEATURE:
<223> OTHER INFORMATION: Primer

<400> SEQUENCE: 60
agcggcgcct ggtgcccacg cgccacttta agagcggcat tag    43

<210> SEQ ID NO 61
<211> LENGTH: 43
<212> TYPE: DNA
<213> ORGANISM: Artificial Sequence
<220> FEATURE:
<223> OTHER INFORMATION: Primer

<400> SEQUENCE: 61
agcggcgcct ggtgcccacg gcacacttta agagcggcat tag    43

<210> SEQ ID NO 62
<211> LENGTH: 43
<212> TYPE: DNA
<213> ORGANISM: Artificial Sequence
<220> FEATURE:
<223> OTHER INFORMATION: Primer

<400> SEQUENCE: 62
agcggcgcct ggtgcccacg ttccacttta agagcggcat tag    43

<210> SEQ ID NO 63
<211> LENGTH: 43
<212> TYPE: DNA
<213> ORGANISM: Artificial Sequence
<220> FEATURE:
<223> OTHER INFORMATION: Primer

<400> SEQUENCE: 63
agcggcgcct ggtgcccacg aaacacttta agagcggcat tag    43

<210> SEQ ID NO 64
<211> LENGTH: 43
<212> TYPE: DNA
<213> ORGANISM: Artificial Sequence -continued
<220> FEATURE:
<223> OTHER INFORMATION: Primer

<400> SEQUENCE: 64
agcggcgcct ggtgcccacg gcccacttta agagcggcat tag      43

<210> SEQ ID NO 65
<211> LENGTH: 43
<212> TYPE: DNA
<213> ORGANISM: Artificial Sequence
<220> FEATURE:
<223> OTHER INFORMATION: Primer

<400> SEQUENCE: 65
agcggcgcct ggtgcccacg atgcacttta agagcggcat tag      43

<210> SEQ ID NO 66
<211> LENGTH: 43
<212> TYPE: DNA
<213> ORGANISM: Artificial Sequence
<220> FEATURE:
<223> OTHER INFORMATION: Primer

<400> SEQUENCE: 66
agcggcgcct ggtgcccacg aatcacttta agagcggcat tag      43

<210> SEQ ID NO 67
<211> LENGTH: 43
<212> TYPE: DNA
<213> ORGANISM: Artificial Sequence
<220> FEATURE:
<223> OTHER INFORMATION: Primer

<400> SEQUENCE: 67
agcggcgcct ggtgcccacg tttcacttta agagcggcat tag      43

<210> SEQ ID NO 68
<211> LENGTH: 43
<212> TYPE: DNA
<213> ORGANISM: Artificial Sequence
<220> FEATURE:
<223> OTHER INFORMATION: Primer

<400> SEQUENCE: 68
agcggcgcct ggtgcccacg cagcacttta agagcggcat tag      43

<210> SEQ ID NO 69
<211> LENGTH: 43
<212> TYPE: DNA
<213> ORGANISM: Artificial Sequence
<220> FEATURE:
<223> OTHER INFORMATION: Primer

<400> SEQUENCE: 69
agcggcgcct ggtgcccacg catcacttta agagcggcat tag      43

<210> SEQ ID NO 70
<211> LENGTH: 43
<212> TYPE: DNA
<213> ORGANISM: Artificial Sequence
<220> FEATURE:
<223> OTHER INFORMATION: Primer

<400> SEQUENCE: 70
agcggcgcct ggtgcccacg gttcacttta agagcggcat tag      43

```
<210> SEQ ID NO 71
<211> LENGTH: 43
<212> TYPE: DNA
<213> ORGANISM: Artificial Sequence
<220> FEATURE:
<223> OTHER INFORMATION: Primer

<400> SEQUENCE: 71
agcggcgcct ggtgcccacg cggcacttta agagcggcat tag          43

<210> SEQ ID NO 72
<211> LENGTH: 43
<212> TYPE: DNA
<213> ORGANISM: Artificial Sequence
<220> FEATURE:
<223> OTHER INFORMATION: Primer

<400> SEQUENCE: 72
agcggcgcct ggtgcccacg ctgcacttta agagcggcat tag          43

<210> SEQ ID NO 73
<211> LENGTH: 43
<212> TYPE: DNA
<213> ORGANISM: Artificial Sequence
<220> FEATURE:
<223> OTHER INFORMATION: Primer

<400> SEQUENCE: 73
agcggcgcct ggtgcccacg acgcacttta agagcggcat tag          43

<210> SEQ ID NO 74
<211> LENGTH: 43
<212> TYPE: DNA
<213> ORGANISM: Artificial Sequence
<220> FEATURE:
<223> OTHER INFORMATION: Primer

<400> SEQUENCE: 74
agcggcgcct ggtgcccacg gctcacttta agagcggcat tag          43

<210> SEQ ID NO 75
<211> LENGTH: 43
<212> TYPE: DNA
<213> ORGANISM: Artificial Sequence
<220> FEATURE:
<223> OTHER INFORMATION: Primer

<400> SEQUENCE: 75
agcggcgcct ggtgcccacg ggtcacttta agagcggcat tag          43

<210> SEQ ID NO 76
<211> LENGTH: 43
<212> TYPE: DNA
<213> ORGANISM: Artificial Sequence
<220> FEATURE:
<223> OTHER INFORMATION: Primer

<400> SEQUENCE: 76
agcggcgcct ggtgcccacg caccacttta agagcggcat tag          43

<210> SEQ ID NO 77
<211> LENGTH: 43
<212> TYPE: DNA
<213> ORGANISM: Artificial Sequence
<220> FEATURE:
<223> OTHER INFORMATION: Primer
```

```
<400> SEQUENCE: 77
agcggcgcct ggtgcccacg ccacacttta agagcggcat tag          43

<210> SEQ ID NO 78
<211> LENGTH: 43
<212> TYPE: DNA
<213> ORGANISM: Artificial Sequence
<220> FEATURE:
<223> OTHER INFORMATION: Primer

<400> SEQUENCE: 78
agcggcgcct ggtgcccacg atacacttta agagcggcat tag          43

<210> SEQ ID NO 79
<211> LENGTH: 43
<212> TYPE: DNA
<213> ORGANISM: Artificial Sequence
<220> FEATURE:
<223> OTHER INFORMATION: Primer

<400> SEQUENCE: 79
aggcgccgct tgcgagcctg tgcggtgttt cagactggga aag          43

<210> SEQ ID NO 80
<211> LENGTH: 43
<212> TYPE: DNA
<213> ORGANISM: Artificial Sequence
<220> FEATURE:
<223> OTHER INFORMATION: Primer

<400> SEQUENCE: 80
aggcgccgct tgcgagcctg gatggtgttt cagactggga aag          43

<210> SEQ ID NO 81
<211> LENGTH: 43
<212> TYPE: DNA
<213> ORGANISM: Artificial Sequence
<220> FEATURE:
<223> OTHER INFORMATION: Primer

<400> SEQUENCE: 81
aggcgccgct tgcgagcctg gaaggtgttt cagactggga aag          43

<210> SEQ ID NO 82
<211> LENGTH: 43
<212> TYPE: DNA
<213> ORGANISM: Artificial Sequence
<220> FEATURE:
<223> OTHER INFORMATION: Primer

<400> SEQUENCE: 82
aggcgccgct tgcgagcctg tttggtgttt cagactggga aag          43

<210> SEQ ID NO 83
<211> LENGTH: 43
<212> TYPE: DNA
<213> ORGANISM: Artificial Sequence
<220> FEATURE:
<223> OTHER INFORMATION: Primer

<400> SEQUENCE: 83
aggcgccgct tgcgagcctg ggcggtgttt cagactggga aag          43

<210> SEQ ID NO 84
```

```
<211> LENGTH: 43
<212> TYPE: DNA
<213> ORGANISM: Artificial Sequence
<220> FEATURE:
<223> OTHER INFORMATION: Primer

<400> SEQUENCE: 84
aggcgccgct tgcgagcctg catggtgttt cagactggga aag        43

<210> SEQ ID NO 85
<211> LENGTH: 43
<212> TYPE: DNA
<213> ORGANISM: Artificial Sequence
<220> FEATURE:
<223> OTHER INFORMATION: Primer

<400> SEQUENCE: 85
aggcgccgct tgcgagcctg attggtgttt cagactggga aag        43

<210> SEQ ID NO 86
<211> LENGTH: 43
<212> TYPE: DNA
<213> ORGANISM: Artificial Sequence
<220> FEATURE:
<223> OTHER INFORMATION: Primer

<400> SEQUENCE: 86
aggcgccgct tgcgagcctg aaaggtgttt cagactggga aag        43

<210> SEQ ID NO 87
<211> LENGTH: 43
<212> TYPE: DNA
<213> ORGANISM: Artificial Sequence
<220> FEATURE:
<223> OTHER INFORMATION: Primer

<400> SEQUENCE: 87
aggcgccgct tgcgagcctg ctgggtgttt cagactggga aag        43

<210> SEQ ID NO 88
<211> LENGTH: 43
<212> TYPE: DNA
<213> ORGANISM: Artificial Sequence
<220> FEATURE:
<223> OTHER INFORMATION: Primer

<400> SEQUENCE: 88
aggcgccgct tgcgagcctg atgggtgttt cagactggga aag        43

<210> SEQ ID NO 89
<211> LENGTH: 43
<212> TYPE: DNA
<213> ORGANISM: Artificial Sequence
<220> FEATURE:
<223> OTHER INFORMATION: Primer

<400> SEQUENCE: 89
aggcgccgct tgcgagcctg aacggtgttt cagactggga aag        43

<210> SEQ ID NO 90
<211> LENGTH: 43
<212> TYPE: DNA
<213> ORGANISM: Artificial Sequence
<220> FEATURE:
<223> OTHER INFORMATION: Primer

<400> SEQUENCE: 90
```
aggcgccgct tgcgagcctg ccgggtgttt cagactggga aag                43

<210> SEQ ID NO 91
<211> LENGTH: 43
<212> TYPE: DNA
<213> ORGANISM: Artificial Sequence
<220> FEATURE:
<223> OTHER INFORMATION: Primer

<400> SEQUENCE: 91
aggcgccgct tgcgagcctg cagggtgttt cagactggga aag                43

<210> SEQ ID NO 92
<211> LENGTH: 43
<212> TYPE: DNA
<213> ORGANISM: Artificial Sequence
<220> FEATURE:
<223> OTHER INFORMATION: Primer

<400> SEQUENCE: 92
aggcgccgct tgcgagcctg cgtggtgttt cagactggga aag                43

<210> SEQ ID NO 93
<211> LENGTH: 43
<212> TYPE: DNA
<213> ORGANISM: Artificial Sequence
<220> FEATURE:
<223> OTHER INFORMATION: Primer

<400> SEQUENCE: 93
aggcgccgct tgcgagcctg agcggtgttt cagactggga aag                43

<210> SEQ ID NO 94
<211> LENGTH: 43
<212> TYPE: DNA
<213> ORGANISM: Artificial Sequence
<220> FEATURE:
<223> OTHER INFORMATION: Primer

<400> SEQUENCE: 94
aggcgccgct tgcgagcctg accggtgttt cagactggga aag                43

<210> SEQ ID NO 95
<211> LENGTH: 43
<212> TYPE: DNA
<213> ORGANISM: Artificial Sequence
<220> FEATURE:
<223> OTHER INFORMATION: Primer

<400> SEQUENCE: 95
aggcgccgct tgcgagcctg gtgggtgttt cagactggga aag                43

<210> SEQ ID NO 96
<211> LENGTH: 43
<212> TYPE: DNA
<213> ORGANISM: Artificial Sequence
<220> FEATURE:
<223> OTHER INFORMATION: Primer

<400> SEQUENCE: 96
aggcgccgct tgcgagcctg tgggtgttt cagactggga aag                 43

<210> SEQ ID NO 97
<211> LENGTH: 43
<212> TYPE: DNA

```
<213> ORGANISM: Artificial Sequence
<220> FEATURE:
<223> OTHER INFORMATION: Primer

<400> SEQUENCE: 97
aggcgccgct tgcgagcctg tatggtgttt cagactggga aag         43

<210> SEQ ID NO 98
<211> LENGTH: 43
<212> TYPE: DNA
<213> ORGANISM: Artificial Sequence
<220> FEATURE:
<223> OTHER INFORMATION: Primer

<400> SEQUENCE: 98
aggctttccc agtctgaaac cgccgccagg ctcgcaagcg gcg         43

<210> SEQ ID NO 99
<211> LENGTH: 43
<212> TYPE: DNA
<213> ORGANISM: Artificial Sequence
<220> FEATURE:
<223> OTHER INFORMATION: Primer

<400> SEQUENCE: 99
aggctttccc agtctgaaac gcacgccagg ctcgcaagcg gcg         43

<210> SEQ ID NO 100
<211> LENGTH: 43
<212> TYPE: DNA
<213> ORGANISM: Artificial Sequence
<220> FEATURE:
<223> OTHER INFORMATION: Primer

<400> SEQUENCE: 100
aggctttccc agtctgaaac atccgccagg ctcgcaagcg gcg         43

<210> SEQ ID NO 101
<211> LENGTH: 43
<212> TYPE: DNA
<213> ORGANISM: Artificial Sequence
<220> FEATURE:
<223> OTHER INFORMATION: Primer

<400> SEQUENCE: 101
aggctttccc agtctgaaac ttccgccagg ctcgcaagcg gcg         43

<210> SEQ ID NO 102
<211> LENGTH: 43
<212> TYPE: DNA
<213> ORGANISM: Artificial Sequence
<220> FEATURE:
<223> OTHER INFORMATION: Primer

<400> SEQUENCE: 102
aggctttccc agtctgaaac aaacgccagg ctcgcaagcg gcg         43

<210> SEQ ID NO 103
<211> LENGTH: 43
<212> TYPE: DNA
<213> ORGANISM: Artificial Sequence
<220> FEATURE:
<223> OTHER INFORMATION: Primer

<400> SEQUENCE: 103
aggctttccc agtctgaaac atgcgccagg ctcgcaagcg gcg         43
```

```
<210> SEQ ID NO 104
<211> LENGTH: 43
<212> TYPE: DNA
<213> ORGANISM: Artificial Sequence
<220> FEATURE:
<223> OTHER INFORMATION: Primer

<400> SEQUENCE: 104
aggctttccc agtctgaaac aatcgccagg ctcgcaagcg gcg          43

<210> SEQ ID NO 105
<211> LENGTH: 43
<212> TYPE: DNA
<213> ORGANISM: Artificial Sequence
<220> FEATURE:
<223> OTHER INFORMATION: Primer

<400> SEQUENCE: 105
aggctttccc agtctgaaac tttcgccagg ctcgcaagcg gcg          43

<210> SEQ ID NO 106
<211> LENGTH: 43
<212> TYPE: DNA
<213> ORGANISM: Artificial Sequence
<220> FEATURE:
<223> OTHER INFORMATION: Primer

<400> SEQUENCE: 106
aggctttccc agtctgaaac cagcgccagg ctcgcaagcg gcg          43

<210> SEQ ID NO 107
<211> LENGTH: 43
<212> TYPE: DNA
<213> ORGANISM: Artificial Sequence
<220> FEATURE:
<223> OTHER INFORMATION: Primer

<400> SEQUENCE: 107
aggctttccc agtctgaaac catcgccagg ctcgcaagcg gcg          43

<210> SEQ ID NO 108
<211> LENGTH: 43
<212> TYPE: DNA
<213> ORGANISM: Artificial Sequence
<220> FEATURE:
<223> OTHER INFORMATION: Primer

<400> SEQUENCE: 108
aggctttccc agtctgaaac gttcgccagg ctcgcaagcg gcg          43

<210> SEQ ID NO 109
<211> LENGTH: 43
<212> TYPE: DNA
<213> ORGANISM: Artificial Sequence
<220> FEATURE:
<223> OTHER INFORMATION: Primer

<400> SEQUENCE: 109
aggctttccc agtctgaaac cggcgccagg ctcgcaagcg gcg          43

<210> SEQ ID NO 110
<211> LENGTH: 43
<212> TYPE: DNA
<213> ORGANISM: Artificial Sequence
<220> FEATURE:
```

<223> OTHER INFORMATION: Primer

<400> SEQUENCE: 110
aggctttccc agtctgaaac ctgcgccagg ctcgcaagcg gcg    43

<210> SEQ ID NO 111
<211> LENGTH: 43
<212> TYPE: DNA
<213> ORGANISM: Artificial Sequence
<220> FEATURE:
<223> OTHER INFORMATION: Primer

<400> SEQUENCE: 111
aggctttccc agtctgaaac acgcgccagg ctcgcaagcg gcg    43

<210> SEQ ID NO 112
<211> LENGTH: 43
<212> TYPE: DNA
<213> ORGANISM: Artificial Sequence
<220> FEATURE:
<223> OTHER INFORMATION: Primer

<400> SEQUENCE: 112
aggctttccc agtctgaaac gctcgccagg ctcgcaagcg gcg    43

<210> SEQ ID NO 113
<211> LENGTH: 43
<212> TYPE: DNA
<213> ORGANISM: Artificial Sequence
<220> FEATURE:
<223> OTHER INFORMATION: Primer

<400> SEQUENCE: 113
aggctttccc agtctgaaac ggtcgccagg ctcgcaagcg gcg    43

<210> SEQ ID NO 114
<211> LENGTH: 43
<212> TYPE: DNA
<213> ORGANISM: Artificial Sequence
<220> FEATURE:
<223> OTHER INFORMATION: Primer

<400> SEQUENCE: 114
aggctttccc agtctgaaac caccgccagg ctcgcaagcg gcg    43

<210> SEQ ID NO 115
<211> LENGTH: 43
<212> TYPE: DNA
<213> ORGANISM: Artificial Seqeunce
<220> FEATURE:
<223> OTHER INFORMATION: Primer

<400> SEQUENCE: 115
aggctttccc agtctgaaac ccacgccagg ctcgcaagcg gcg    43

<210> SEQ ID NO 116
<211> LENGTH: 43
<212> TYPE: DNA
<213> ORGANISM: Artificial Sequence
<220> FEATURE:
<223> OTHER INFORMATION: Primer

<400> SEQUENCE: 116
aggctttccc agtctgaaac atacgccagg ctcgcaagcg gcg    43